United States Patent [19]

Williamson et al.

[11] Patent Number: 5,487,299

[45] Date of Patent: Jan. 30, 1996

[54] APPARATUS AND METHOD FOR DESTRUCTIVE TESTING OF COUPONS FORMED FROM METAL

[75] Inventors: Calvin C. Williamson; Jeffrey S. Salsman, both of Napa, Calif.

[73] Assignee: Napa Pipe Corporation, Napa, Calif.

[21] Appl. No.: 334,819

[22] Filed: Nov. 4, 1994

[51] Int. Cl.$^6$ .................................................. G01P 15/00
[52] U.S. Cl. ...................................... 73/12.09; 73/12.13
[58] Field of Search ............................... 73/12.01, 12.04, 73/12.06, 12.07, 12.09, 12.12, 12.13

[56] References Cited

U.S. PATENT DOCUMENTS

| | | | |
|---|---|---|---|
| 4,495,587 | 1/1985 | Plante et al. | 73/602 |
| 4,648,264 | 3/1987 | Freese et al. | 73/64.41 |
| 5,392,652 | 2/1995 | Levesque et al. | 73/629 |

*Primary Examiner*—Richard Chilcot
*Assistant Examiner*—Max Noori
*Attorney, Agent, or Firm*—Bernhard Kreten

[57] ABSTRACT

An apparatus and method for conducting destructive testing is disclosed. A flywheel 14 supports a hammer 60 on an outer periphery thereof and in fixed position relative thereto. A carriage 90 includes a support mechanism which supports a coupon C taken from an article of manufacture. The carriage 90 moves between a first retracted position and a second deployed position. In the deployed position, the coupon C is placed into the path of the hammer 60 as the flywheel 14 rotates. Sensing means 200 are provided for sequencing the advancement of the coupon C into the hammer's path. Means are provided for disengaging a drive which powers the flywheel 14 immediately prior to the hammer 60 impacting and severing the coupon C. Means are further provided for measuring the decrement in flywheel speed caused by severing the coupon C. The decrement can be related to the force required in passing the hammer 60 through the coupon C which in turn relates to thez properties of material forming the coupon C.

24 Claims, 14 Drawing Sheets

APPARATUS AND METHOD FOR DESTRUCTIVE TESTING OF COUPONS FORMED FROM METAL

FIELD OF THE INVENTION

This invention relates generally to an instrumentality which is used to test the quality of articles of manufacture. More specifically, an instrumentality is disclosed which couples a hammer to a flywheel in which rotation of the flywheel to a specific velocity signals when it is appropriate for a coupon to be advanced in the path of the hammer for destructive testing. The quality of the coupon and therefore a pipe from which the coupon has been removed correlates with an indication of quality for a batch of metal from which the pipe was formed so that a decrease in the velocity measured at the flywheel could provide further indicia as to brittleness or ductility of the coupon and therefore the batch.

BACKGROUND OF THE INVENTION

Gas pipe lines have been transmitting compressible substances at increasingly higher pressures over the past several years. Notable improvements in the integrity and strength of pipes which carry the compressed gas are the single most important factor in allowing gas to be transported at ever increasing pressures.

Consequently, as the ability of pipes to carry greater through-put increases, there also arises a need to provide more sophisticated testing equipment to assure that the quality of the pipes is maintained at these elevated pressures. Traditionally, pipe coupons have been first cut from production-line pipes and then tested with a pendulum-type drop weight tear test machine. The pendulum is dependent upon a specific mass falling by gravity through a known distance to attain a calculated velocity as it reaches its lowest point where its energy is greatest.

The following documents reflect the state of the art of which applicants are aware and are included herewith to discharge applicants' acknowledged duty to disclose relevant prior art. It is stipulated, however, that none of these documents teach singly nor render obvious when considered in any conceivable combination the nexus of the instant invention as hereinafter claimed.

| U.S. PAT. NO. | ISSUE DATE | INVENTOR |
|---|---|---|
| 1,201,326 | October 17, 1916 | Matsumura |
| 1,414,427 | May 2, 1922 | Lynch |
| 1,462,813 | July 24, 1923 | McAdam |
| 1,604,141 | October 26, 1926 | Amsler |
| 1,984,904 | December 18, 1934 | Warshaw, et al. |
| 2,022,666 | December 3, 1935 | Haskell, et al. |
| 2,067,140 | January 5, 1937 | Dinzl |
| 2,188,898 | February 6, 1940 | Haskell, et al. |
| 2,323,724 | July 6, 1943 | Nadai, et al. |
| 2,396,620 | March 12, 1946 | Taxwood |
| 2,339,460 | January 18, 1944 | Cozzoli |
| 2,422,317 | June 17, 1947 | Stock, et al. |
| 2,498,291 | February 21, 1950 | Nadai |
| 2,506,607 | May 9, 1950 | McKendry |
| 2,721,971 | October 25, 1955 | Francois |
| 2,728,224 | December 27, 1955 | Wheeler |
| 2,778,219 | January 22, 1957 | Wachter |
| 2,924,969 | February 16, 1960 | Clough, et al. |
| 2,959,051 | November 8, 1960 | Simek, et al. |
| 3,067,605 | December 11, 1962 | Bliss |
| 3,157,046 | November 17, 1964 | Orner |
| 3,192,762 | July 6, 1965 | Muller |
| 3,194,052 | July 13, 1965 | Melzer |
| 3,209,585 | October 5, 1965 | Wolstenholme, et al. |
| 3,285,060 | November 15, 1966 | Pessen |
| 3,365,938 | January 30, 1968 | Matsushita, et al. |
| 3,376,736 | April 9, 1968 | Emery, Jr. |
| 3,665,749 | May 30, 1972 | Brenner |
| 3,985,015 | October 12, 1976 | Rice |
| 4,418,564 | December 6, 1983 | McKinley |
| 4,537,060 | August 27, 1985 | Underwood |
| 4,546,654 | October 15, 1985 | Isherwood, et al. |
| 5,277,055 | January 11, 1994 | Pittard, et al. |

| FOREIGN PATENT DOCUMENTS | | | | | |
|---|---|---|---|---|---|
| DOCUMENT NUMBER | DATE | NAME | CLASS | SUB-CLASS* | FILING DATE |
| Russian 198,757 | 08/1967 | | | | |

OTHER PRIOR ART (Including Author, Title, Date, Pertinent Pages, Etc.)

American Petroleum Institute; API Recommended Practice for Conducting Drop-Weight Tear Tests on Line Pipe; Second edition, March, 1978; complete edition.

Memory Devices, Ltd.; Analog Devices; date unknown, Chapter 1, pages 1 through 10.

The patents to Wachter, Orner and Pessen each describe classic pendulum-type impact testers in which a hammer is caused to swing through an arc and impacts a specimen at a known velocity computed by knowing such variables as the weight of the hammer, the distance through the arc that it travels and the point of impact. Once the hammer passes through the specimen, its subsequent travel against gravity is noted and can be correlated directly to the force imparted in fracturing the specimen.

As technological advances have been made in metallurgy, fabrication methodology and heat treating, and, in view of the gross magnitude of larger diameter pipes having greater wall thicknesses, pendulum-type testers would have to become geometrically much larger than those presently existing.

It should be observed that the anchoring mechanism which holds the specimen in this type of testing environment must also be quite substantial to assure no deleterious effect on the test itself. For example if the system were to flex and then "rebound", accuracy could be compromised. From an engineering perspective, while it is entirely possible to scale-up to a larger pendulum-type tester, the requirements in greater physical space and the associated costs may make it more impractical for pipe testing of this nature to occur at the site where the pipes are being formed because for example, of increases in support structure. If one were to centralize the testing site, shipping of the pipe specimens and coupons to a remote testing site inefficiently resolves the problem.

Testing standards have been established by the American Petroleum Institute which outline recommended processes for conducting drop-weight tear tests on pipe which many pipe purchasers can specify when placing pipe orders. For example, after sheets of steel are formed into pipe, the pipe can be tested by cutting out two coupons per "heat" (typically every 50 to 300 tons). When coupons are successfully tested, the process of cutting coupons from sections of a pipe to conduct subsequent destructive testing of the coupon would result in substantially greater costs if the coupons have to be shipped to a remote site that has the capability of fracturing the larger pipe coupon with the larger drop-type pendulum tester. Thus, a need exists for an improved pipe tester which occupies a relatively modest amount of space and is economical to allow on site testing of the coupons at the pipe forming facility.

The patent to Nadai, et al. (U.S. Pat. No. 2,323,724, issued Jul. 6, 1943) teaches the use of a high velocity tensile machine or high speed impact machine coupled with measuring anti recording means for obtaining stress/strain characteristics with regard to a changing force either with reference to time or as a function of displacement. A flywheel, driven by a direct current motor (2), supports a pair of hammers pivotably mounted on and rotating with the flywheel. The hammers are pinned to the flywheel (1) by means of pins (14) around which the hammer can be rotated. A trigger (15) releases the hammers to allow them to rotate into a striking position where they abut against a stop by means of a spring (16) attached to the flywheel. Thus, a spring biased lever (20) is partially rotated so as to unlatch the hammer thereby moving the latter from the position shown in dotted lines to that which is shown in full lines. The trigger (15) is tripped by a solenoid operated pin (21) actuateable by means of solenoid (22). Solenoid (22) moves pin (21) so as to rotate trigger (15) clockwise to thus rotate lever (20) counter clockwise to thus release the hammers (3) and (4). When the hammers are in an extended, deployed position, they are oriented to contact an anvil (12) which depends from a test specimen (8) which in turn depends from a force measuring bar (9). The force measuring bar (9) is thermally isolated from the test specimen (8) by means of a cooling plug (11) through which a suitable cooling liquid flows (FIG. 3). The cooling plug (11) prevents overheating of the force measuring bar (9) because the specimen (8) is heated in a furnace (13) which moves from a first position where heat is transferred to the specimen to a second position where the specimen is subsequently tested.

The patent to Nadai, 2,498,291, issued Feb. 21, 1950, discloses that improvements were made on the earlier patent based on the observation that oscillations set up by striking the specimen resulted in undesirable maximum and minimum peaks in the initial portion of the resultant stress/strain curve. Accordingly, resilient materials (17, 17') are disposed respectively in both the anvil (10) and the hammer (4) in an attempt at attenuating the effect of the "rebound" which disturbs the readings desired.

The remaining citations show the state of the art further and diverge more starkly from the instant invention as delineated hereinafter.

SUMMARY OF THE INVENTION

The instant invention is distinguished over the known prior art in a multiplicity of ways. A flywheel supports a hammer such that the hammer is held in a fixed position. The hammer is exposed beyond the outer periphery of the flywheel and remains deployed at all times. The effect of positioning the hammer outboard the flywheel is negated by the removal of material immediately adjacent the hammer. Thus supporting the hammer on the flywheel by removal of flywheel material renders negligible any issues with respect to balancing and vibration of the flywheel.

The present invention includes a carriage which supports a coupon in a first retracted position, away from the path of the flywheel and away from the path of the hammer. Sensing means are provided strategically to note both the position of the hammer and the speed at which the hammer travels. Once the hammer and flywheel have been powered to a desired speed, the sensing means notes when the hammer will have just cleared the location of the carriage.

Means for advancing the carriage from a first retracted position to a second deployed position are provided upon the hammer's having gone past the carriage. The coupon mounted in the carriage is then oriented and held in fixed relationship with respect to the path that the hammer travels so that upon one revolution, the hammer impacts the coupon. The flywheel speed and other geometry associated with the apparatus of the present invention have been strategically calculated to ensure that the hammer passes through the coupon, severing the coupon into two portions. Immediately prior to the hammer contacting the coupon, the hammer and flywheel are disengaged from the motor which powers the flywheel so that the inherent kinetic energy of the flywheel and hammer are the sole motive forces acting upon the coupon.

The force required to fracture the coupon results in a decrease in the velocity of the hammer and the flywheel. This decrement in the velocity of the hammer and flywheel is measured by sensing means. Computational means are operatively coupled to the sensing means for converting the decrement in velocity to the amount of energy which was required to fracture the coupon. Means are also provided for reinitialization so that a different coupon can be inserted in the carriage for subsequent tests.

OBJECTS OF THE INVENTION

Accordingly, it is a primary object of the present invention to provide a new and novel apparatus and method for testing the quality of material by fracturing coupons under the influence of an impact means.

It is further object of the present invention to provide a device as characterized above which is extremely durable in construction, safe to use and highly reliable in operation.

A further object of the present invention is to provide a device as characterized above which keeps pace with advances in metallurgy and ever increasing dimensions of wall thickness and pipe diameter in the steel industry.

It is a further object of the present invention to provide a device as characterized above which includes sensing means for accurately and reliably receiving subsequent specimens to be tested.

A further object of the present invention is to provide a method for testing pipe.

A further object of the present invention is to provide a device as characterized above which records the results of those coupon tests so that a machine and method will have been provided which promulgates rapid throughput of testing products.

Viewed from a first vantage point, it is an object of the present invention to provide an apparatus for destructive testing of a coupon formed from metal, in which a flywheel having an outer periphery supports a hammer coupled to the flywheel and extending beyond the outer periphery, a carriage means, means for moving the carriage means from a first retracted position to a second deployed position, coupon supporting means disposed on the carriage means and sensing means allowing the coupon to be moved to the second deployed position, whereby in the second deployed position, the coupon is placed in the path of the hammer.

Viewed from a second vantage point, it is an object of the present invention to provide a pipe tester for determining the structural integrity of pipe by removing a coupon from a representative sample of pipe and tear testing the coupon, comprising, in combination coupon support means, hammer means, hammer powering means coupled to the hammer means to cause the hammer means to achieve a known velocity, means for moving the coupon support means into contact with the hammer means once the hammer means reaches the known velocity, means to disable the hammer powering means just prior to contacting the coupon.

Viewed from a third vantage point, it is an object of the present invention to provide a method for testing the structural integrity of material having a directional grain which correlates with a potential line of failure of the material, the steps including obtaining a specimen of the material to be tested, orienting the directional grain of the specimen so that the directional grain is exposed to a force in excess of that required for failure, rotating a force applying means, placing the specimen in the path of the force applying means, and measuring the force required to pass through the specimen.

These and other objects will be made manifest when considering the following detailed specification when taken in conjunction with the appended drawing figures.

DESCRIPTION OF PREFERRED EMBODIMENTS

Figure 1:
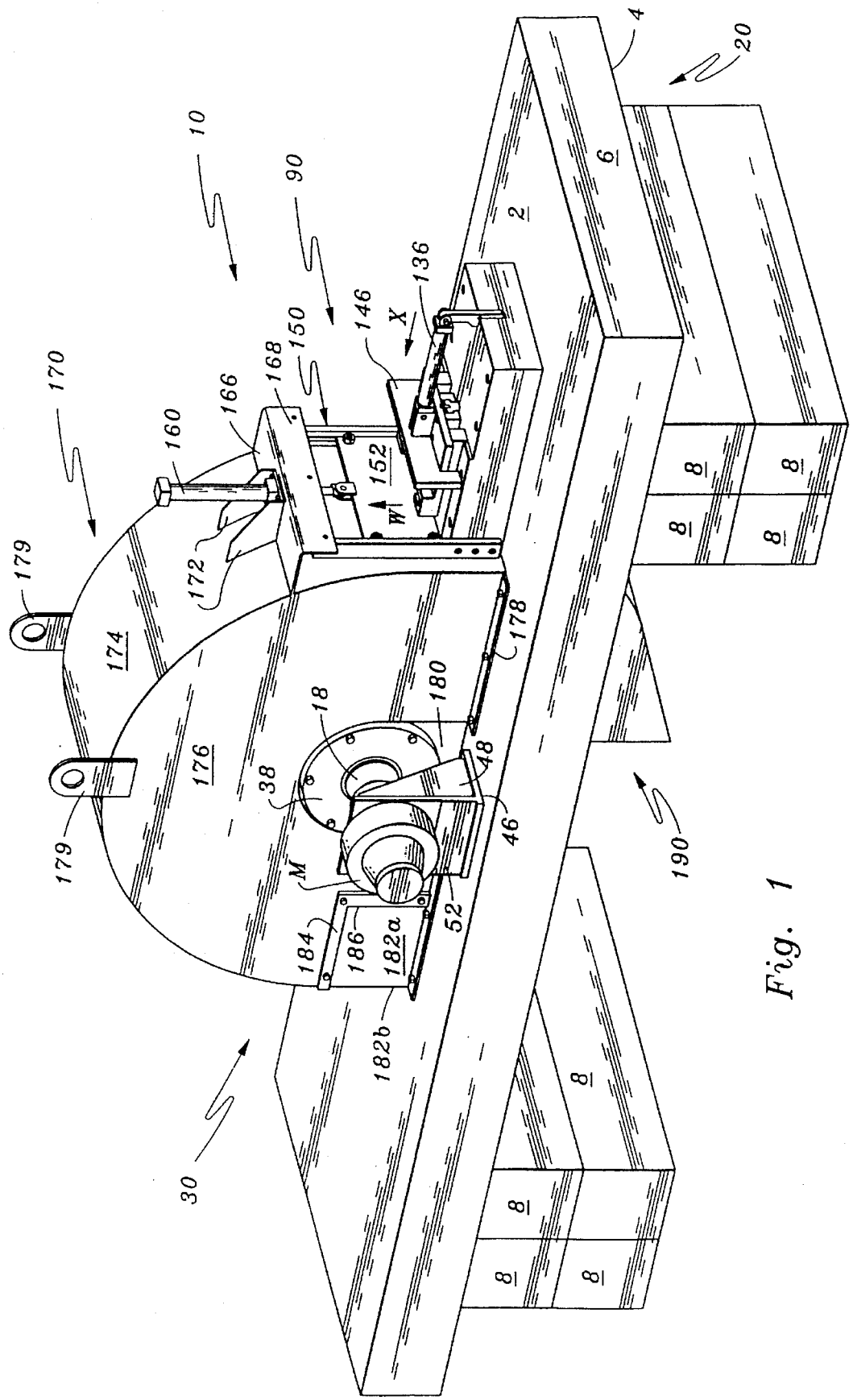
FIG. 1 is a perspective view showing the apparatus of the present invention.

Considering the drawings, wherein like reference numerals denote like parts throughout the various figures, reference numeral 10 is directed to the apparatus for destructive testing of coupons.

In its essence, the coupon testing apparatus 10 (FIGS. 1 through 3) includes a support stand 30 upon which a flywheel 14 is rotatably supported. One sector of the flywheel, at its outer periphery, supports a hammer 60 formed in a recess provided in the flywheel 14. A shield 170, 190 occludes the flywheel and hammer assembly and is supported on the stand 30. The stand 30 includes a table 20 having a top surface 2 located below the axis of rotation of the flywheel 14. The shield has an upper cowling 170 which includes a gate 152 which opens and closes allowing access to the hammer 60. A carriage 90 is supported on the table 20 and includes a support sled 130 to receive a coupon C to be tested. Means 136 to move the coupon C and its coupon support sled 130 from a first retracted position (outside the shield) to a second deployed position (within the interior of the shield) are provided such that the coupon C addresses the hammer 60 as it moves in its trajectory so that the coupon C can be torn by the hammer. Means 200 are also provided for sensing the decrement in flywheel speed that is attributable to the hammer 60 having passed through the coupon C. Means M for maintaining the rotation of the hammer 60 and the flywheel 14 at a certain predetermined velocity prior to striking the coupon C is also provided.

More specifically, and with reference to FIG. 1, details of the coupon testing apparatus are explored. The apparatus 10 is elevated above the ground by means of a stand 30. The stand 30 includes a table 20 having a horizontally supported planar upper surface 2, a corresponding parallel lower surface 4 and a peripheral edge 6 interposed between the upper surface 2 and the lower surface 4. The table's planar surface is preferably formed as a solid steel monolith in which an initial prototype is approximately ten inches thick. That is, the distance between the upper surface 2 and the lower surface 4 is ten inches. The horizontally supported planar surface is formed substantially as a rectangle. The table 20 includes legs 8 extending between the lower surface 4 of the table and the ground. The legs 8 are formed from solid masses of wood configured as elongate rectangular blanks. As shown, the legs 8 are formed from four blocks of wood, stacked in a two by two array.

Figure 3:
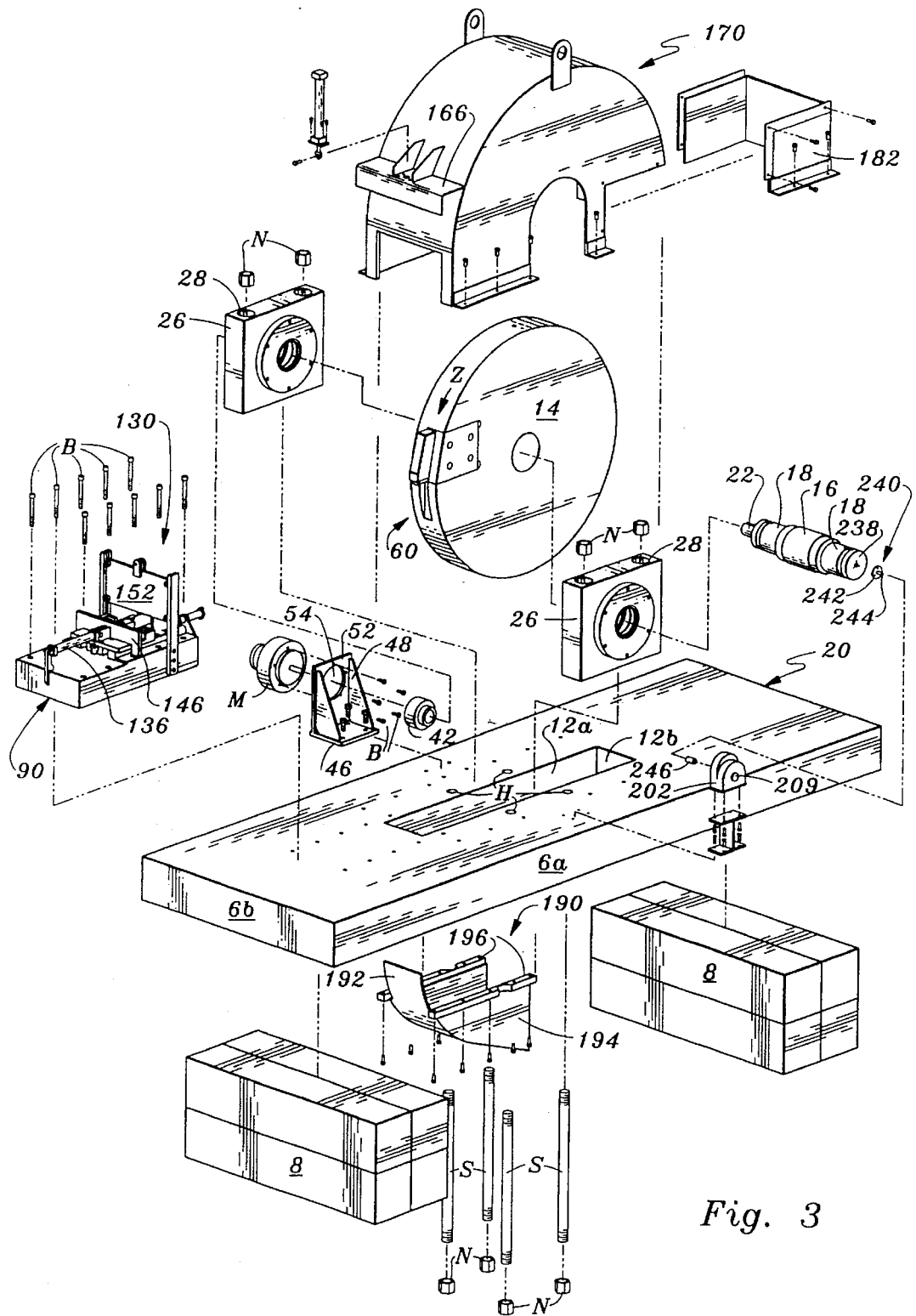
FIG. 3 is an exploded parts perspective view of that which is shown in FIG. 1.

FIG. 3 reflects that the table 20 includes a central cut-out 12 passing through the horizontally supported planar upper surface 2 and lower surface 4. The cut-out 12 is centrally disposed and is a substantially elongate rectangular cut-out having longitudinal sides 12a parallel with longitudinal edges 6a of the table 20 and latitudinal sides 12b parallel latitudinal edges 6b of the table.

Figure 2:
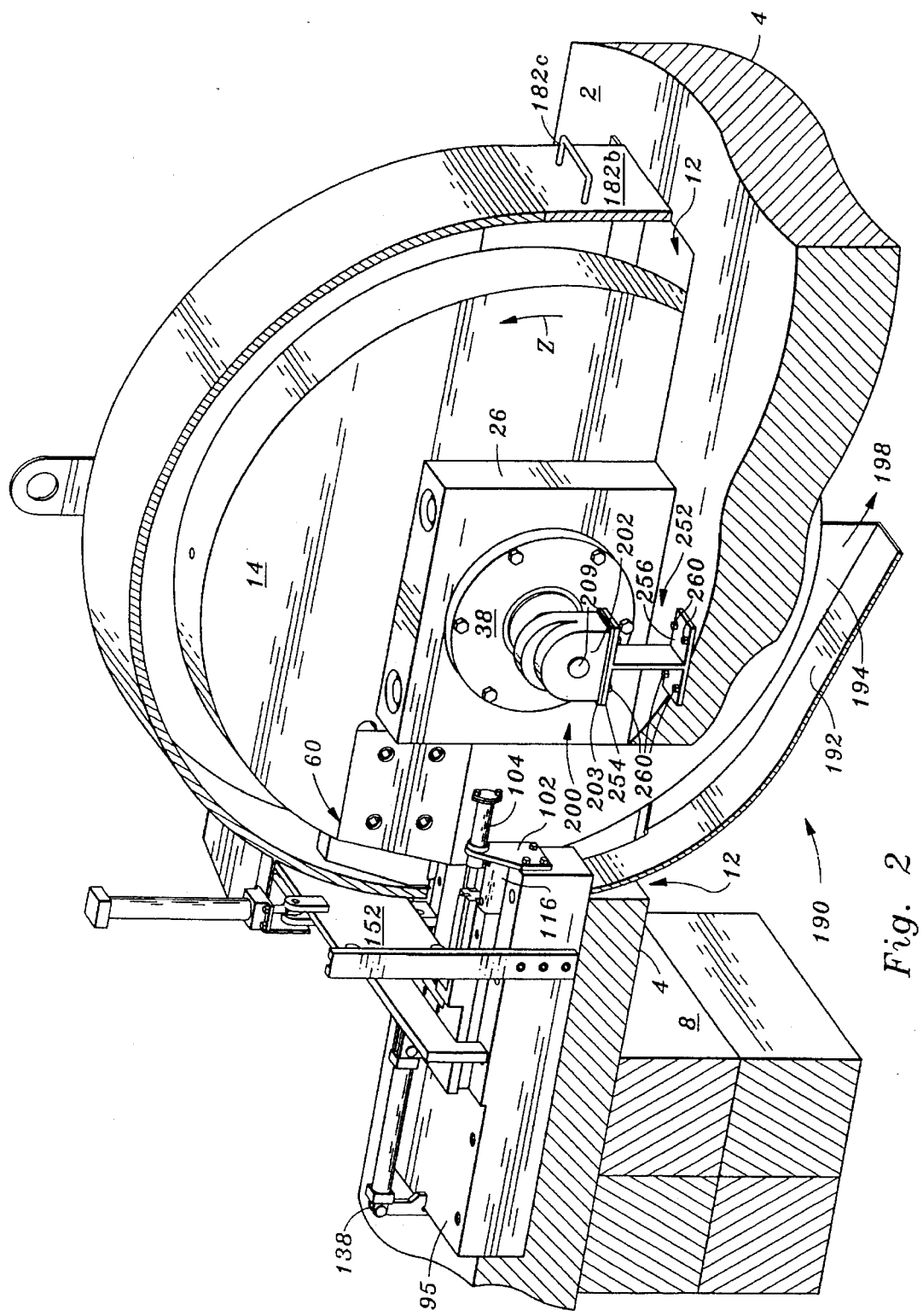
FIG. 2 is partial view of the apparatus in section.

Force applying means is generally shown in FIGS. 1 through 3. In its essence, it includes the flywheel 14 and a motor M which drives the hammer 60 in the direction of the arrow "Z". The flywheel 14 is supported on a flywheel shaft 16. The shaft 16 includes bearing support surfaces 18 of a somewhat lesser diameter and outboard the central diameter which is used to support the flywheel 14.

Figure 6:
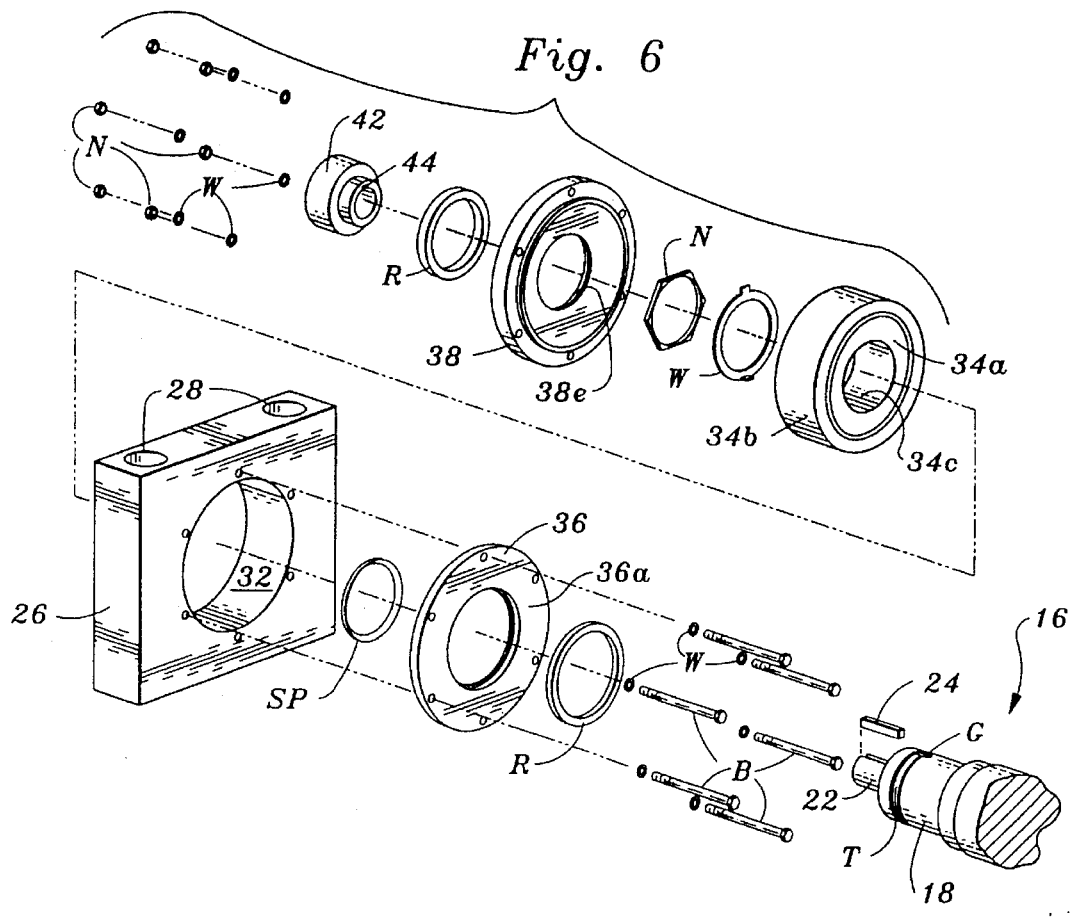
FIG. 6 is another exploded parts perspective view.

Referring to FIG. 6, the shaft 16 further includes a driving end 22 which receives input from the motor M by means of shaft coupler 42. A key way 44 found in coupler 42 communicates with and drives a key 24 which is contained within a slot complementally formed on the end 22 of shaft 16. Each bearing support surface 18 resides within a bearing block 26 that has a horizontal inner bore 32 and a pair of vertically disposed bores 28 that fasten the bearing block onto the table 20.

The vertical bores 28 (FIG. 3) communicate with studs S having nuts N at opposed threaded extremities. The studs S communicate with holes H that pass through the upper and lower surfaces 2, 4 of table 20 and allow the bearing blocks 26 to be firmly affixed thereto.

The inner bore 32 (FIG. 6) of the bearing block has a periphery. complemental to an outer diameter of an outer race 34b of bearing 34. Thus, the outer race 34b of the bearing 34 frictionally resides within the inner bore 32 of the bearing block 26. An inner race 34a of the bearing 34 has a central bore 34c complemental to the diameter of the bearing support surfaces 18 of the flywheel shaft 16. Thus, the flywheel 14 is supported in rotational engagement with the bearings 34 to allow rotation of the flywheel 14 along the direction of the arrow "Z" shown in FIG. 3.

An inner bearing plate 36 is interposed between each bearing block and the flywheel. An outer bearing plate 38 is on a side of the bearing block 26 opposite from the inner bearing plate 36. A side 36a of each inner bearing plate 36 includes a sealing ring R adapted to frictionally reside over a portion of the shaft 16 sandwiching the inner bearing plate thereat. A spacer SP is located on an opposite side of each inner bearing plate 36.

A nut N abuts against bearing 34 through washer W. The outer bearing plate 38 abuts against bearing block 26. This nut N and washer W reside respectively on a threaded portion T and groove C formed just outboard the bearing support surface 18 of the shaft 16 that helps to positively locate the bearing 34 with respect to the shaft 16 and prevent axial migration. A recess 38e is formed adjacent an outer surface (i.e. nearest coupler 42) of the outer bearing plate 38 and the recess receives a sealing ring R. The inner and outer bearing plates 36, 38 are sandwiched to the bearing block 26 by means of a plurality of bolts B and nuts N, each bolt and nut including a washer W to help lock the bolts and nuts together.

Figure 5:
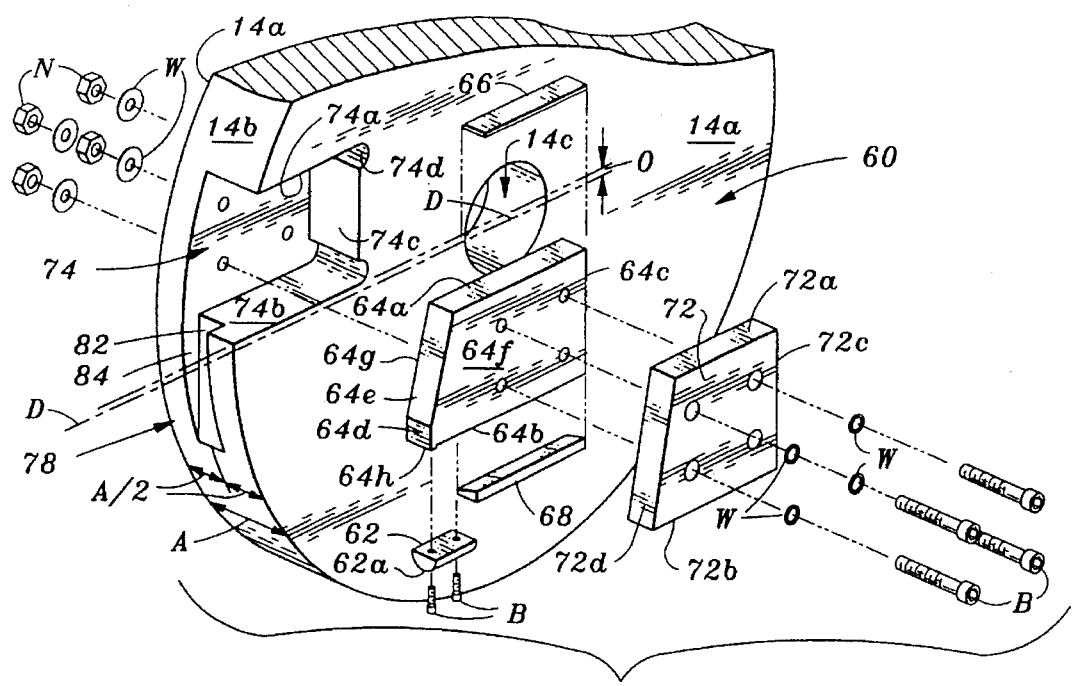
FIG. 5 is another exploded parts perspective view.

Referring to FIGS. 1 and 3, the coupler 42 allows the motor M to drive the shaft 16 and flywheel 14. The motor M is supported on a projection that includes a base 46, a pair of spaced parallel triangularly-shaped gussets 48 extending upwardly from the base 46 on opposed side edges of the base 46. The gussets 48 are oriented adjacent one outer edge of the base 46 to help support a face plate 52 extending upwardly from one edge of the base 46. The face plate 52 is provided with an opening 54 allowing access of the motor M to the coupler 42 and therefore the driving end 22 of the shaft 16. The motor M is supported on the face plate 52 and the motor base 46 is supported on the upper surface 2 of the table 20 by means of a plurality of bolts B. One hydraulic motor which appears to be satisfactory for the intended purpose is manufactured by Vickers, part number HMB010. Thus, rotation of the motor M will cause rotation of the flywheel 14 along the direction of the arrow "Z". As mentioned, the flywheel 14 supports a hammer 60 thereon. FIG. 3 and especially FIG. 5 provide details of the hammer structure and its relationship to the flywheel 14. The flywheel 14 is a substantially disc-shaped solid metallic mass, including a pair of circular side faces 14a communicating with an annular band 14b which connects peripheral edges of the circular side faces 14a. A central bore 14c allows the shaft 16 to drive the flywheel 14. The bore 14c is located at the geometrical center of the flywheel 14.

One portion of the band 14b of the flywheel and on one side face thereof supports a hammer 60 (please see FIG. 5). The hammer 60 includes a nose 62 having a contact surface that in section is substantially U-shaped. The nose 62 is connected to a nose anchor 64. The nose anchor 64 is a seven-sided solid having an upper surface 64a and lower surface 64b, an inner surface 64c perpendicular to the upper surface 64a, a "beak" portion 64d adjacent the nose 62 which is perpendicular to the upper surface 64a, and a truncated portion 64e communicating from the "beak" portion 64d adjacent the nose 62 to the upper surface 64a. Note that the "beak" portion 64d includes a lip 64h to capture a front wall 62a of the nose 62. Planar front 64f and rear 64g walls complete the seven-sided solid. The lower surface 64b is canted compared to upper surface 64a for purposes to be assigned.

A recess 74 is formed in the flywheel 14 complemental to the nose anchor 64. Specifically, an anchor recess 74 has a horizontal upper wall 74a and a parallel lower wall 74b to receive the upper and lower surfaces of the nose anchor 64 in frictional engagement therewith. However, the nose anchor 64 is preferably separated from the anchor recess walls 74a and 74b by means of an upper shim 66 and a lower wedge shaped shim 68. These shims are formed from non-elastic, rigid, hardened material. Shim 68 wedges against the cant of lower surface 64b so that a lower surface of shim 68 is parallel to upper surface 64a. A back wall 74c of the anchor recess 74 allows the inner surface 64c of the nose anchor to abut thereagainst. The anchor recess 74 is provided with relief areas 74d at the intersection of the corners of the upper wall 74a and lower wall 74b with the back wall 74c. The relief area 74d is formed during milling and provides stress relief at the transition between walls 74a, 74b and 74c.

The nose anchor 64 is fixed on the flywheel 14 by means of a hammer retaining plate 72 of substantially trapezoidal configuration and having a top wall 72a complemental to the anchor recess upper wall 74a, a bottom wall 72b complemental to the anchor recess lower wall 74b, a back wall 72c complemental to the anchor recess back wall 74c, and a front wall 72d oriented at an oblique angle with respect to the top 72a and bottom 72b walls.

Although the nose 62 projects out beyond an outer peripheral band 14b of the flywheel 14, an undercut 78 is provided on the flywheel band 14b adjacent the nose 62. More particularly, the undercut 78 is formed to include a ramp 82 which slopes inwardly from the outer band 14b of the flywheel 14. The ramp communicates with the anchor recess lower wall 74b. The ramp 82 is symmetrically formed defined by a central vertical plane of the flywheel parallel to its side faces 14a. The ramp 82 communicates with ramp walls 84 on either side thereof. Ramp 82 transitions to the outer band 14b of the flywheel 14.

The hammer surface of the nose 62 is disposed along a diameter D of the flywheel 14 while the anchor recess lower wall 74b is off-set therefrom by a dimension O shown in FIG. 5. Also, it is preferred that the U-shaped contour of the nose 62 be symmetrically disposed on the outer band 14b of the flywheel 14 so that the flywheel has a thickness A and the bottom of the nose is equally distant (A/2) from either side of the flywheel 14.

Details with respect to the mechanism by which the coupon C is advanced into the path of the nose 62 can now be explored. FIG. 3 reflects that a carriage 90 attaches to the table 20 by means of a multiplicity of bolts B passing through the carriage and into the table 20. In order for the coupon C to be advanced from a first retracted position to a second deployed position, a gate 152 must open along the direction of the arrow "W" (FIG. 1) and the coupon must be advanced towards the hammer in the direction of the arrow "X".

Figure 4:
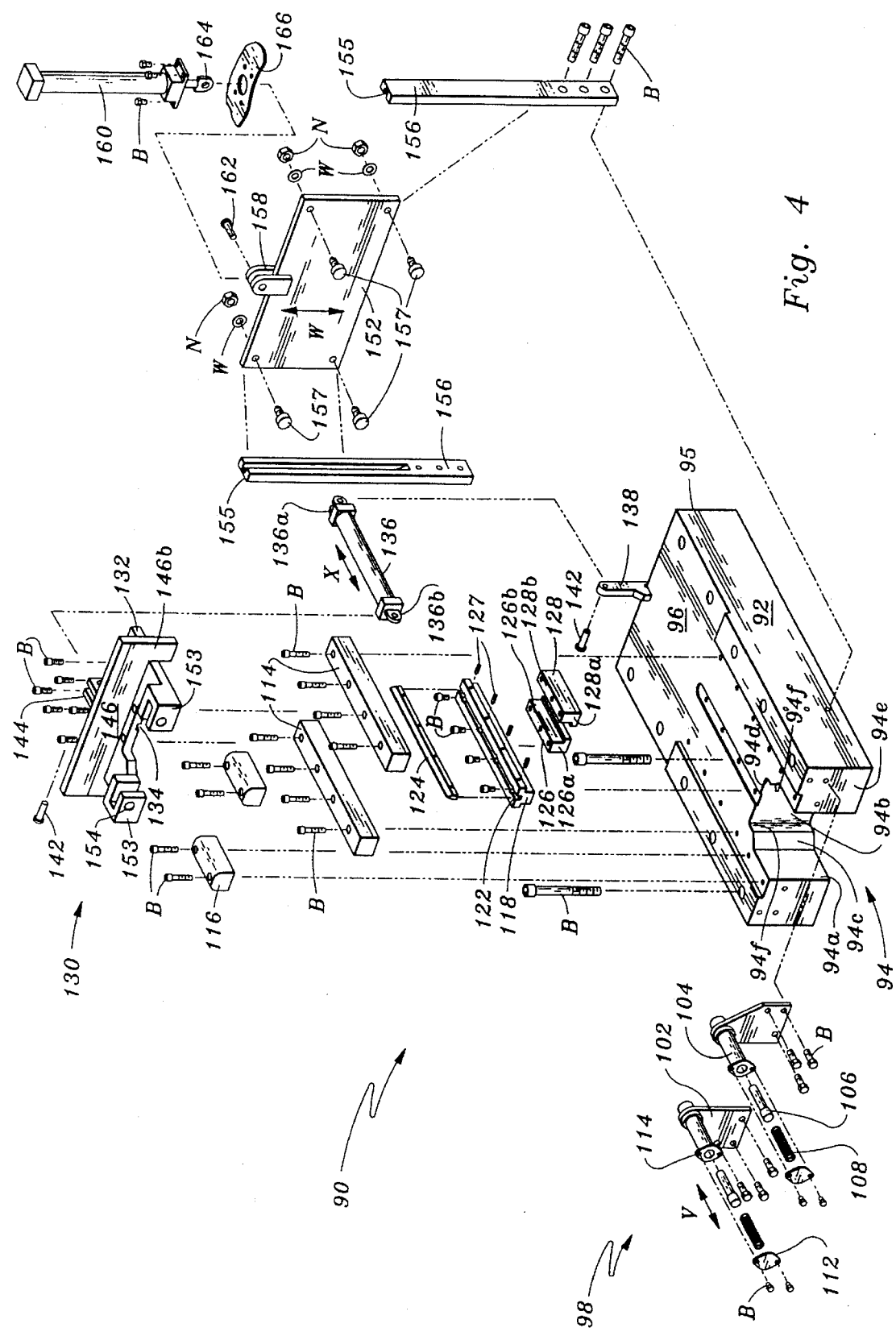
FIG. 4 is exploded parts perspective view of a carriage.

FIG. 4 provides the requisite details of the carriage 90. A platform 92 includes a top surface 96, and an end 94. The platform end 94 includes a recess defined by a bight portion 94b, a pair of legs 94a emanating from the bight portion 94b and a chamfer 94c extending between the legs 94a and the bight 94b. In addition, a radiused area 94d provides a transition between the chamfer 94c and the bight 94b. A linear clearance section 94f exists between each chamfer 94c and radiused area 94d. Clearance section 94f is dimensioned to allow the nose 62 of the hammer 60 to pass therebetween. The legs 94a include feet 94e. These feet 94e support a pair of coupon orienting-devices 98.

In essence, each leg 94a at its foot 94e supports a tang 102 extending upwardly from each foot 94e. The tangs 102 allow tang sleeves 104 to project and straddle either side of the flywheel 14 on a side remote from the carriage platform 92. The sleeves 104 permit the coupons to be oriented properly by means of coupon pins 106 which reciprocate along the direction of the double ended arrow "V" against spring pressure caused by spring 108 supported in the sleeve 104 and held in the sleeve by means of an end wall 112 which seals the sleeve 104 and provides tension in conjunction with the spring 108. Optionally, one or more of the pins 106 could be coupled with a limit switch to indicate the presence of the coupon in abutting relationship against the pin, as will be described.

Figure 15:
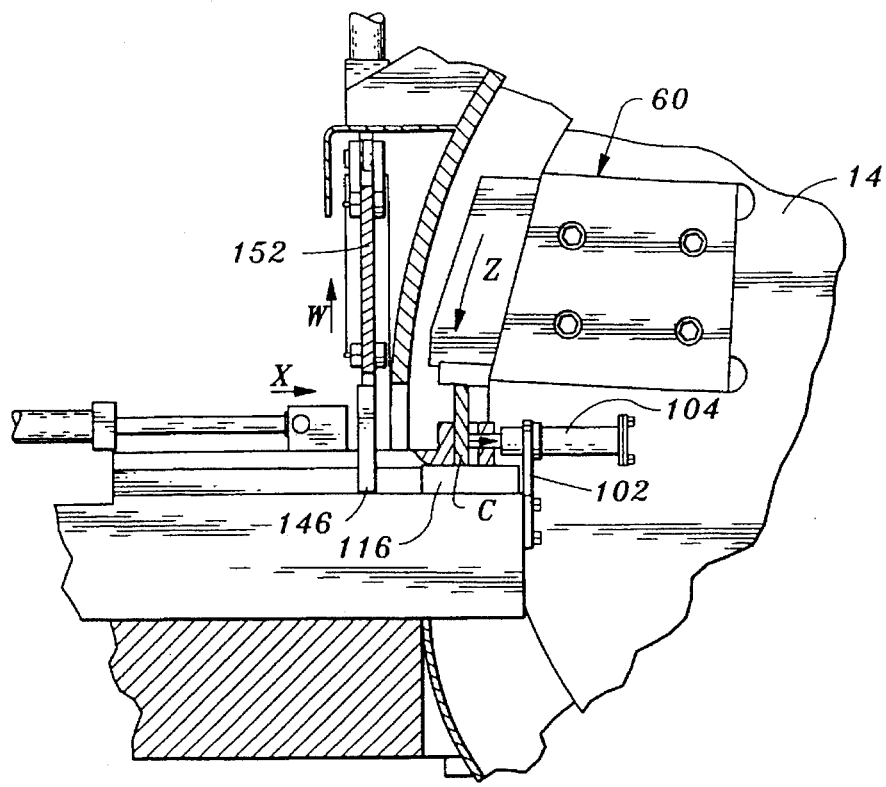
FIG. 15 is a side view of that which is shown in FIGS. 12 and 13, but at impact.

The top 96 of the platform 92 includes a pair of spaced parallel elongate rails 114 attached to the top surface of the platform by a plurality of bolts B. In addition, the top rails 114 are axially aligned with anvils 116 which terminate adjacent the feet 94e of the platform end 94. The anvils 116 have an outer contour radiused to provide a smooth transition from the legs 94a of the platform 94 as it transitions to the anvils 116. This radius coacts with the coupon at fracture. FIG. 15 shows that the anvils 116 are spaced from a face of tang 102 opposite from the side of the sleeve 104.

A track 118 (FIG. 4) having a substantially T-shaped cross-section and an elongate extent is fixed to the top surface 96 of the platform 92 by a plurality of bolts B. The track 118 has a longitudinally extending groove 122 provided on a top surface thereof within which a rail 124 is secured by means of grub screws 127. A pair of inwardly facing. L-shaped travelers 126, 128 face each other and are constrained to operate along the length of the track 118 by having horizontal legs 126a, 128a of the L-shaped travelers underlie a shelf portion on the horizontal underside of the T-shaped track 118.

A top surface of each of the travelers 126b, 128b fastens to an under side of a coupon sled 130. The coupon sled 130 provides a means to support the coupon as it advances from a first retracted position to a second deployed position which is in the path of the hammer 60. As shown in FIG. 4, the sled 130 attaches to the travelers 126, 128 by a plurality of bolts B passing through a foundation 132 of the sled. An underside of the sled also includes a runner 134 provided with clearance from the rail 124 carried on a top face of the T-shaped track 118. Linear motion of the sled 130 along the direction of the arrow "X" is preordained by the travelers 126, 128 coaction with the track 118.

A hydraulic cylinder 136 is used to move the sled 130 with respect to the carriage 90. The hydraulic cylinder 136 could be mounting style BB manufactured by Parker. One end 136a of the hydraulic cylinder 136 attaches to an end 95 of the carriage platform 92 remote from the platform end 94 by means of a clevis 138 that receives a pin 142 to fix the cylinder 136. An opposite end 136b of the cylinder 136 attaches to the sled 130 by means of another pin 142 which passes through a pair of ears 144, capturing the cylinder's end 136b therebetween. The ears 144 are supported on a top surface of the foundation 132 at its intersection with a sled barrier 146.

Figure 13:
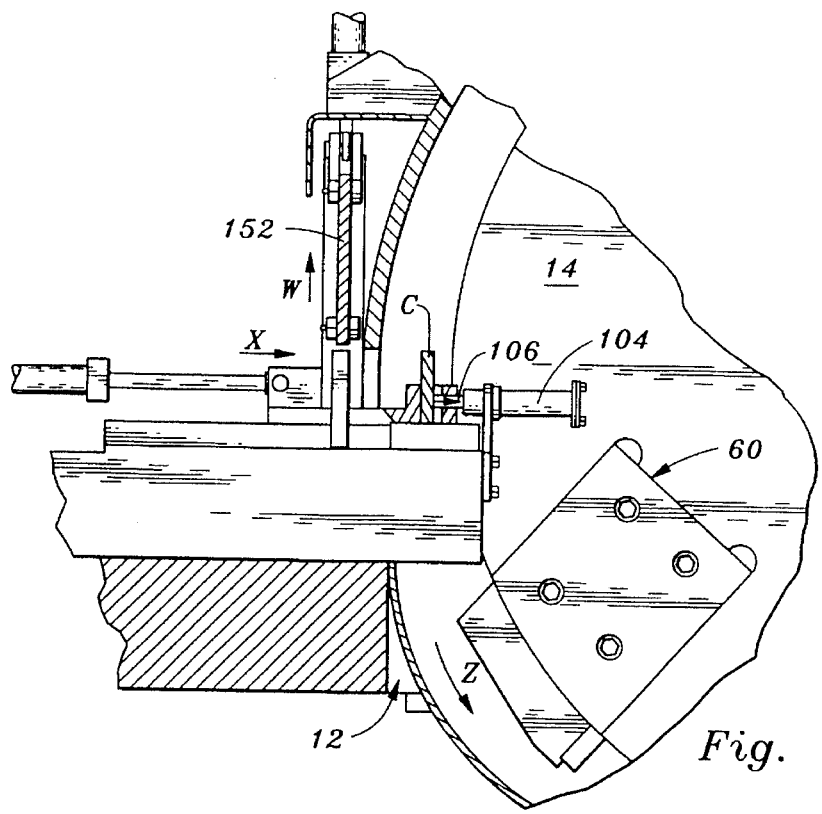
FIG. 13 is a side view allowing coupon advancement.

The sled barrier 146 is a downwardly extending U-shaped member having legs 146b which extend down and straddle side edges of the foundation 132. During the test procedure, the sled barrier 146 supplements the safety provided by gate 152 to be described hereinafter. A forward portion of the sled includes two inwardly facing U-shaped members 153 at a forwardmost portion of the foundation 132. These inwardly facing U-shaped members 153 define a coupon support cradle. Please see FIG. 11. Thus, bight portions 148 of the coupon support face each other as do the coupon support legs 153 so that a coupon C is placed between each of the bight portions and is straddled by the legs 153, with the coupon C resting on a top surface of the rails 114 and subsequently the anvils 116. The coupon support legs 153 that are on a side closest the flywheel both have a hole 154 passing therethrough dimensioned to contact and receive the pins 106 that support the coupon located on the platform end 94 of the carriage 90. FIG. 13 shows the pin 106 being retracted under spring pressure caused by the placement of the coupon C thereagainst. Note that the rail 124 projects into the coupon as shall be described.

As mentioned, the sled barrier 146 occludes access to the flywheel when the coupon C is being fragmented. However, the coupon is not permitted to advance into the flywheel area unless and until a safety gate mechanism 150 has been opened. As shown diagramatically in FIG. 1, for example, a gate 152 can move in the direction of the arrow "W" in order to allow the coupon C access to an interior portion of the device 10 containing the flywheel 14. The flywheel 14 is totally ensconced in a shield having an upper cowl 170 and lower cowl 190 to be discussed. With the gate 152 in an open position (e.g. FIG. 13) the coupon C is properly oriented for testing by impact with the nose 62 of the hammer 60. The gate 152 reciprocates along the direction of the double ended arrows "W" (FIG. 4) and the gate 152 is constrained to operate along those double ended arrows "W" by latitudinal edges thereof being constrained within channelways 156 which have tracks 155. Rollers 157 abut against channelways 156 adjacent the tracks 155. The channelways 156 are secured as uprights by being fastened to side walls of the platform 92 near the platform end 94 so that the gate 152 provides an obstruction limiting access to the flywheel 14. A topmost portion of the gate 152 includes clevis 158 which is attached to one end of a hydraulic cylinder 160 by means of a pin 162. The hydraulic cylinder 160 can be purchased from Parker, Style J, Series 2H. While the one end 164 of the hydraulic cylinder 160 is attached to the clevis 158, a remainder of the outer hydraulic cylinder is supported on a shelf 166 best seen in FIGS. 1 and 3.

The shelf is substantially L-shaped having a horizontal portion 166 and a vertical portion 168 depending downwardly from the horizontal portion 166 at an edge remote from its connection to an upper cowl 170. Gussets 172 extending between the cowling 170 and the shelf 166 enhance the strength of the connection for the hydraulic cylinder 160 to the gate 152.

More specifically, the upper cowl 170 includes an arcuate top wall 174 fixed to a pair of spaced, parallel, inverted U-shaped side walls 176. The side walls 176 and top wall 174 are joined at edges thereby providing a well which overlies the flywheel 14 above the top surface 2 of the table 20. Apertured tangs 179 on side walls 176 facilitate removal of cowl 170. The cowling therefore provides a form of scatter shield. The cowling renders it less likely that a projectile will be propelled beyond the flywheel area. Any projectile shall be contained by the scatter shield. Bottom edges of the side walls of the scatter shield include laterally extending flanges 178 fastened to the table 20. An inverted U-shaped cut-away is provided adjacent the bearing plates 38 for clearance. A U-shaped maintenance portal 182 is located with one leg 182a on each side wall 176 remote from carriage 90, and a bight portion 182b located on a bottom area of the arcuate top wall 174 allowing access to the hammer 60. The U-shaped portal 182 attaches to side walls by reinforcing ribs 184 and 186. Portal 182 includes an access handle 182c to facilitate removal.

Figure 16:
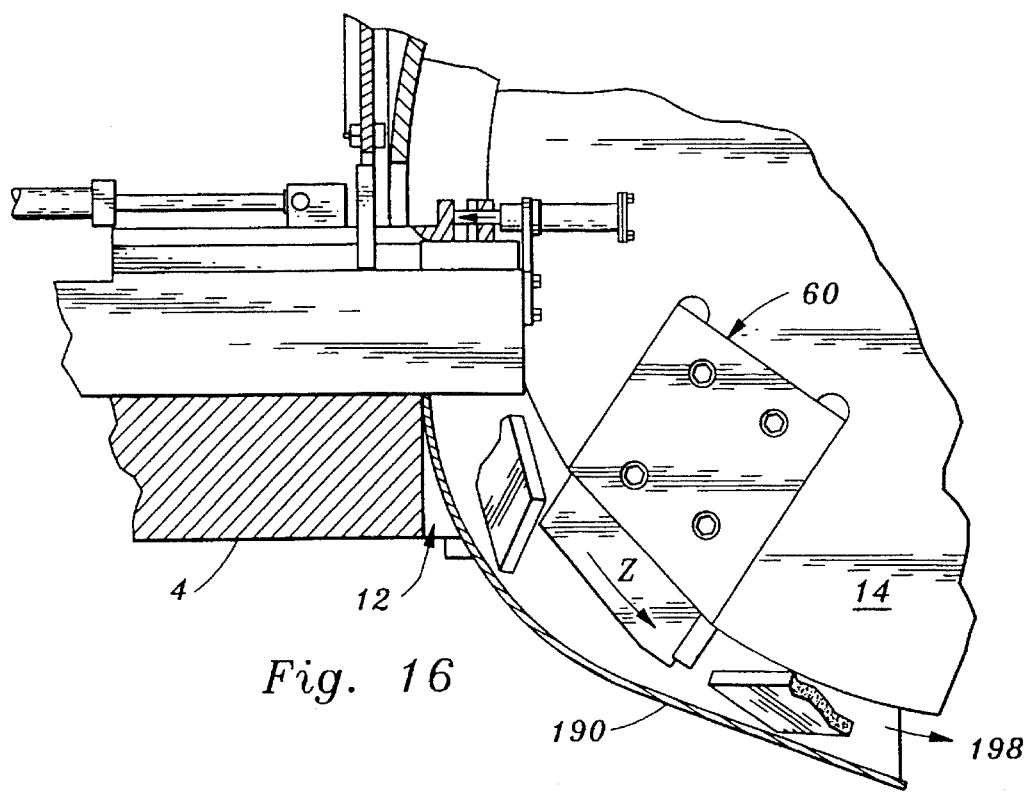
FIG. 16 is a side view of that which is shown in FIGS. 12 and 13, but at post impact.

A lower cowl 190 is also provided on the bottom surface 4 of the table 20. The lower cowl 190 is best seen in FIGS. 1, 2 and 3 and includes a pair of spaced parallel side panels 194 and an arcuate segment 192 connecting the side panels 194. Flanges 196 on edges of the panels 194 attach the lower cowl 190 to the bottom surface 4 of the table 20. The lower cowl 190 also is provided with a discharge chute 198 which allows the fractured coupons to be safely discharged in a controlled manner (FIG. 16).

Figure 11:
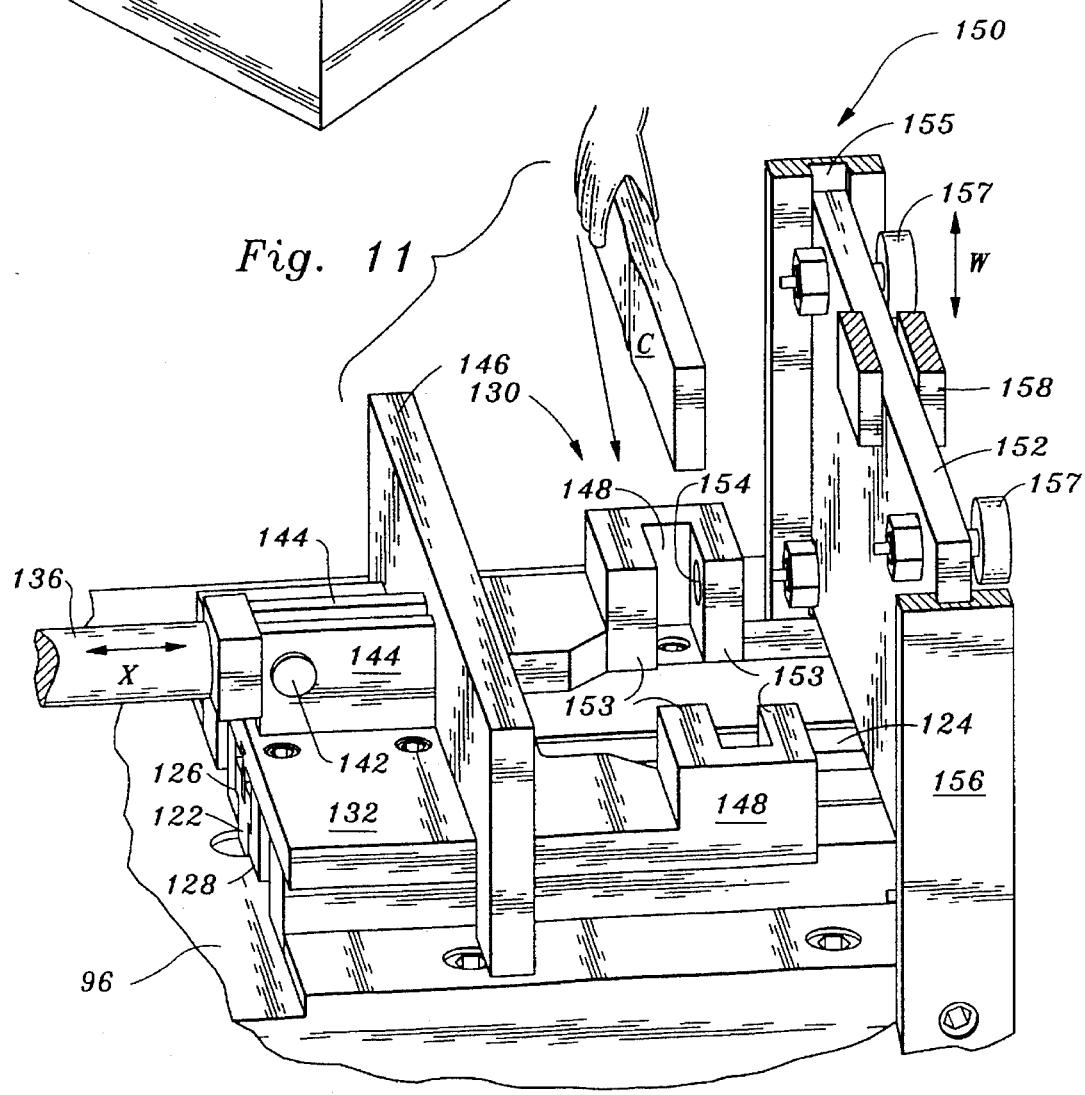
FIG. 11 is a perspective view of the carriage.
Figure 11A:
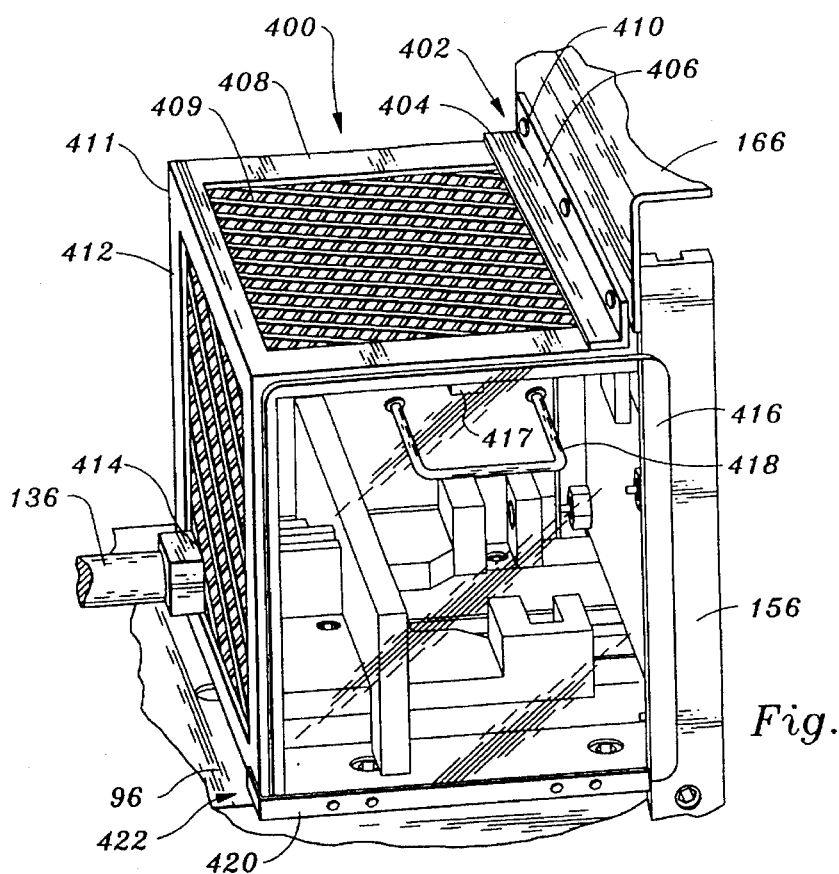
FIG. 11A is a perspective view of a safety cage covering the carriage.

Referring to FIG. 11A, a safety cage 400 may be provided to encompass the sled 130. The safety cage 400 is provided as an additional safety feature which will contain any type of projectile that may be kicked back from the testing area. The safety cage 400 is rigidly fastened to the shelf 166 by way of a substantially L-shaped bracket 402. The L-shaped bracket 402 includes a horizontal portion 404 preferably welded to a top 408 of the safety cage 400. The bracket 402 also includes a vertical portion 406 depending upwardly from the horizontal position 404 and preferably bolted by bolts 410 to the shelf 166.

The cage 400 includes a top wall 409, a side wall 411, a back wall 412 and a side door 416. These walls substantially define the cage. Preferably, all walls except the door are formed from mesh. Note that the back wall 412 of the safety cage 400 is provided with an aperture 414 so that the linear motion of the hydraulic cylinder 136 along the direction of the arrow "X" is unimpeded. The side door 416 includes a handle 418 and is hinged via hinge 420 to a bottom extremity 422 of the cage 400. The side door 416 is formed of clear material and provides access to the sled 130 for placing the coupon C within the sled for testing. A magnetic latch 417 keeps the door secure and may include a sensor which may prevent operation of the device without door closure.

Figures 18, 19:
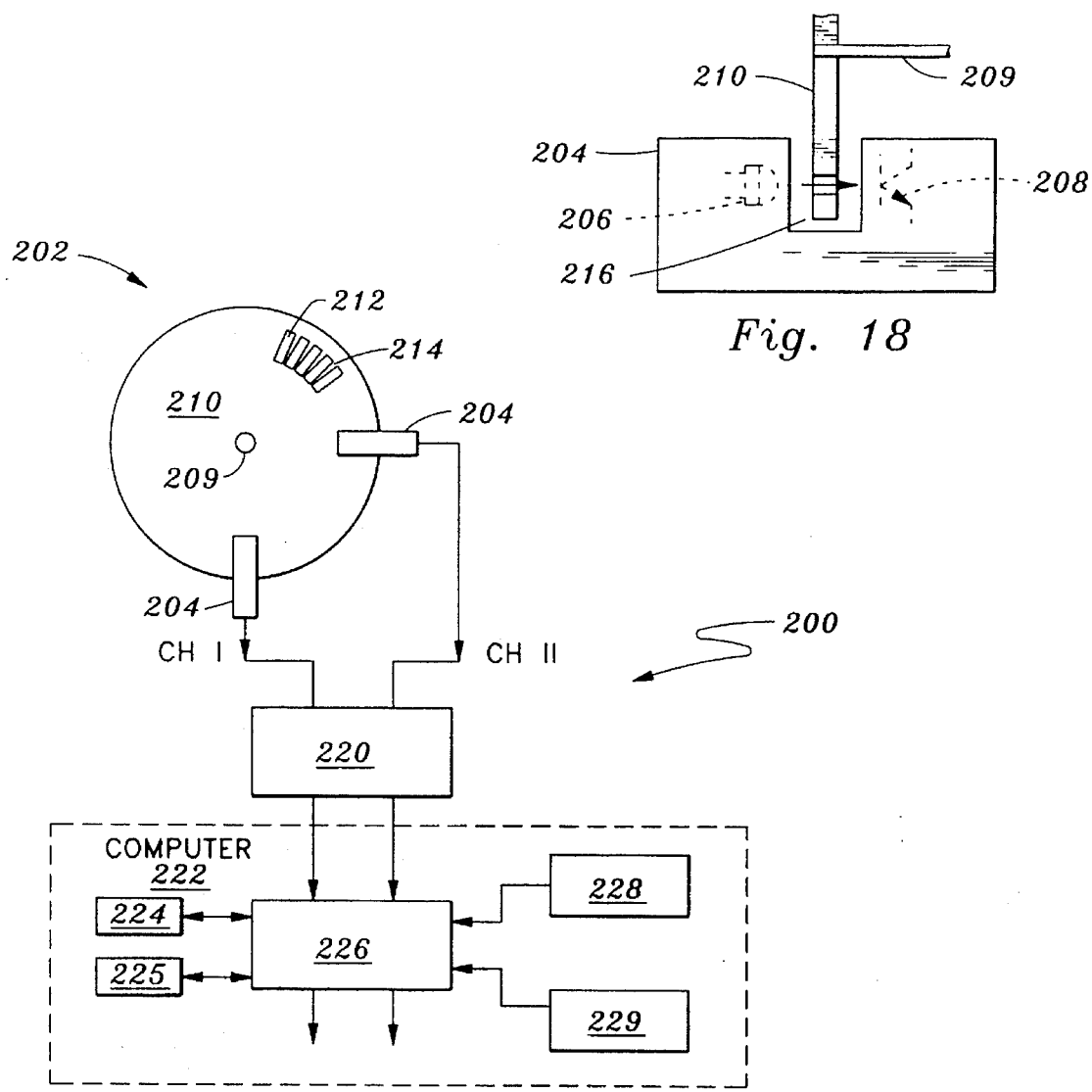
FIG. 18 is a schematic view of one sensor.
FIG. 19 is a schematic view of the encoder and the computer.

Referring to FIG. 19, the means 200 for sensing and measuring both the position of the hammer 60 and the speed at which the hammer 60 travels is accomplished with the use of an encoder 202 and a computer 222.

Referring to FIGS. 2 and 3, the encoder 202 is operatively coupled to the shaft 16 and is supported on the top surface 2 of the table 20 by an I-beam 252. A top 254 of the I-beam 252 is preferably bolted with bolts 260 to the base 203 of the encoder 202. A bottom 256 of the I-beam 252 is also preferably bolted with bolts 260 to the top surface 2 of the table 20. An end 238 of the shaft 16 (FIG. 3) is operatively coupled to a head 242 of a tack 240. A shem 244 of the tack 240 couples to an encoding shaft 209 of the encoder 202 via coupler 246.

Referring to FIGS. 18 and 19, the encoder 202 preferably includes a circuit comprising an optical link 204 formed by a light emitting diode (LED) 206 and a photosensor or phototransistor 208. In addition, a disk 210 is provided which operatively couples to the encoding shaft 209. This disk 210 includes slots 212 cut at regular intervals near its outer periphery. When the shaft 16 (FIG. 3) rotates, the disk 210 rotates partially inside an opening 216 provided between the LED 206 and the photosensor 208 which are facing each other. As the disk 210 rotates, the light from the LED 206 passes through the slots 212 in the disk 210 and is blocked by solid portions 214 of the disk 210. Therefore, the encoder 202 outputs a pulse train whose duty cycle depends on the size and spacing of the slots 212 and whose frequency depends on the speed of the shaft 16.

Figure 20A:
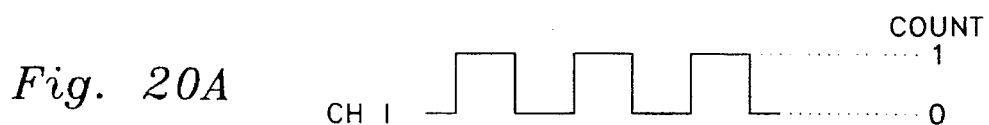
FIG. 20 is a timing diagram of output by the encoder.
Figure 20B:
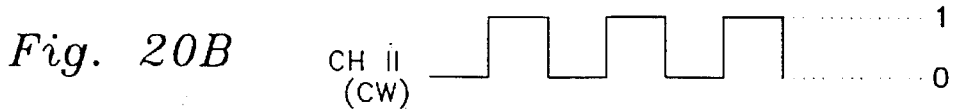
Figure 20C:
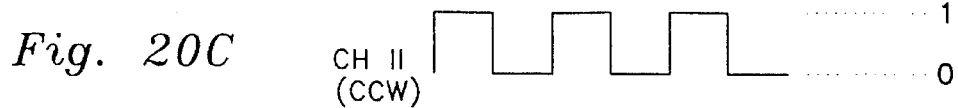

The instant invention uses the encoder 202 in conjunction with a clock 224 preferably located in the computer 222 to measure the velocity of the flywheel 14 (FIG. 3). The flywheel 14 is rotatably supported by the shaft 16 having the end 22 operatively coupled to the motor M. As mentioned, the disk 210 of the encoder 202 is operatively coupled to the opposite end 238 of the shaft 16. The encoder 202 may consist of 2,500 counts or slots 212 per revolution. One of the slots may be opaque to the sensor in order to correlate the encoder to a position of the hammer 60 so that the hammer's location is known at all times. The signal output from the encoder 202 is shown in FIG. 20 and is in a "quadrature" format. Thus, there are two squarewave signals, channel I and channel II. When the shaft 16 of the flywheel 14 is rotating clockwise, channel I leads channel II by 90° and the counter 226 of the computer 222 increases. When the shaft 16 of the flywheel 14 is rotating counterclockwise, channel I lags channel II by 90° and the counter 226 of the computer 222 decreases. This method determines the direction of the flywheel 14, and also the distance traveled by the flywheel 14.

An encoder board 220 multiplies the standard output from the encoder 202 by four. In this case, if the encoder's standard output were 2,500 counts per revolution, the encoder board 220 would therefore count 10,000 counts per revolution. The resolution of the encoder 202 can be determined as follows: The diameter of the flywheel is multiplied by $\pi$ (approximately 3.14) to determine the circumference or the outer periphery distance of the flywheel which is equal to 188.495 inches if the flywheel has a 60 inch diameter. The circumference, 188.495 inches, is divided by 10,000 (which is the counts per revolution of the encoder) resulting in 0.018495 inches per count. The clock signal comes from an 8254 counter/timer chip 226 in the computer 222. A clock rate of 1.193183 megahertz (MHz) is applied by clock 224 to the three inputs of the counter 226 as the clock signal. This frequency is generated from the 14,317,180 hertz crystal provided by clock 224 in the computer 222. This frequency is divided by three to generate the 4.77 MHZ clock signal for the microprocessor and further dividing by four leads to the signal provided to the counter 226.

The counter 226 can be programmed and set-up to run in different modes. The mode that the instant invention concerns itself with is the counter mode. The counter is loaded with 65,535 and when the counter 226 counts down to zero, it reloads and starts over. When the counter 226 reaches zero, the counter 226 generates a hardware interrupt. When this interrupt is serviced, the clock 224 is updated. It does this every 18.2 milliseconds. This is a result of dividing the frequency provided to the counter 226 by the count 65,535.By way of example, if it takes 200 clock-cycles for one encoder count, and the 200 clock-cycles are divided by the frequency of the clock signal from clock 224, the result is 0.000168 seconds. One encoder count equals 0.018495 inches and when divided by the time, (0.000168 seconds) the result is 110 inches per second or 9.16 feet per second, which is the velocity of the flywheel 14.

Figure 21:
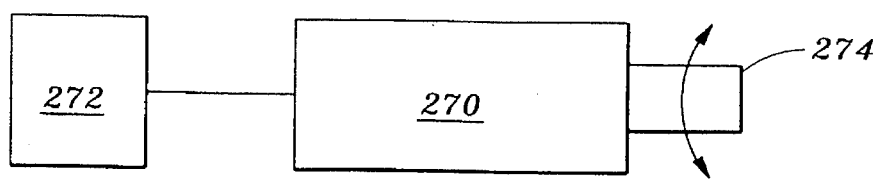
FIG. 21 is a schematic View of the resolver.
Figure 22:
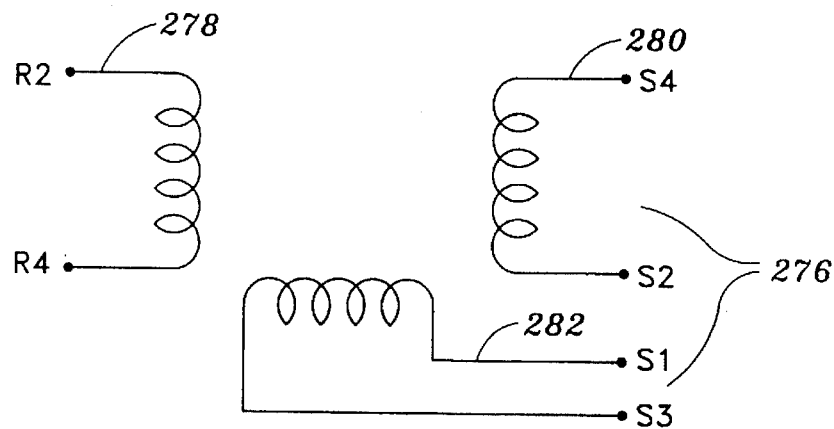
FIG. 22 is a schematic view of the resolver's windings.

Alternatively, and referring to FIGS. 21, a resolver 270 in conjunction with an appropriate interface electronic circuit 272 can form the heart of a digital shaft angle measurement and positioning system. One such resolver is disclosed in the publication "Analog Devices" by Memory Device, Ltd. The resolver 270 is supported on the top surface 2 of the table 20 in the same manner as the encoder 202 and has a shaft 274 operatively coupled to the end 238 of the shaft 16 by way of the coupling 246 and the tack 240. The resolver 270 is a form of a synchro in which the windings on a slave stator 276 and rotor 278 (driven by shaft 16) are displaced mechanically by 90° to each other as schematically shown in FIG. 22 instead of 120° as in the case of synchros. The stator 276 includes at least two windings 280, 282 spaced 90° from each other. The resolver 270, therefore, exploits the sinusoidal relationship between a shaft angle and an output voltage.

Figure 23:
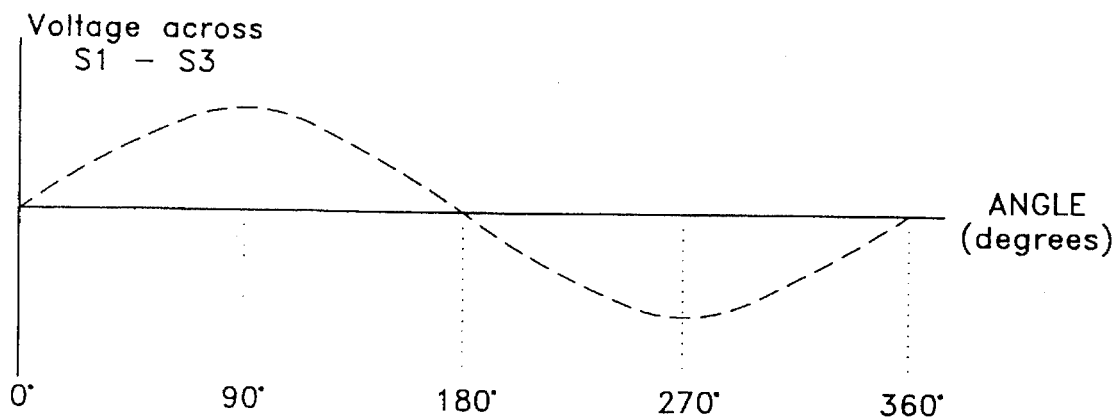
FIG. 23 is a graphical depiction of the resolver's output.

For example, and as shown in FIG. 23 the output voltage of the resolver is a sinewave that is referenced at its beginning with a zero positioning of the shaft, it will reflect the shaft angle from 0° to 360° per cycle of the waveform. More specifically, as the shaft begins its rotation from an initialized referenced zero mark, the output voltage will be a positive increasing portion of the sinewave. The sinewave will continue to increase from a shaft positioning of 0° to 90°, and then start decreasing from 90° to 180°. The sinewave becomes negative after 180° and continues to increase negatively until it reaches 270° where it is still negative, but begins to increase back to a zero position where it repeats the cycle as delineated above. The velocity of the shaft is determined by noting, from the sinewave produced by the resolver, the change in displacement of the shaft and the change in time that it took for the displacement to occur.

Figure 7:
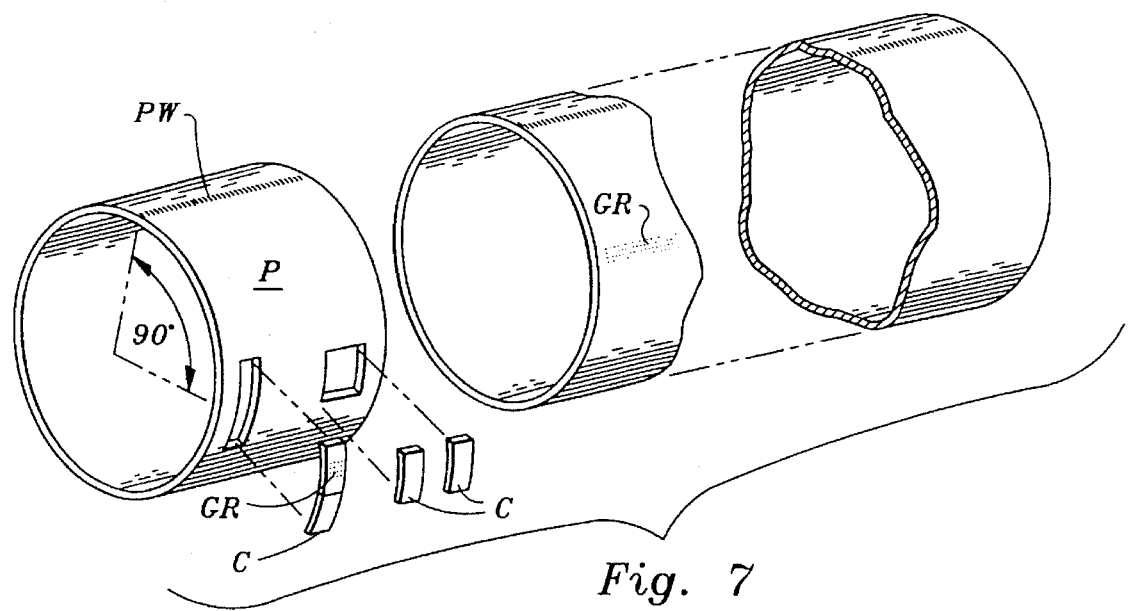
FIG. 7 is a perspective view of pipes.
Figure 8:
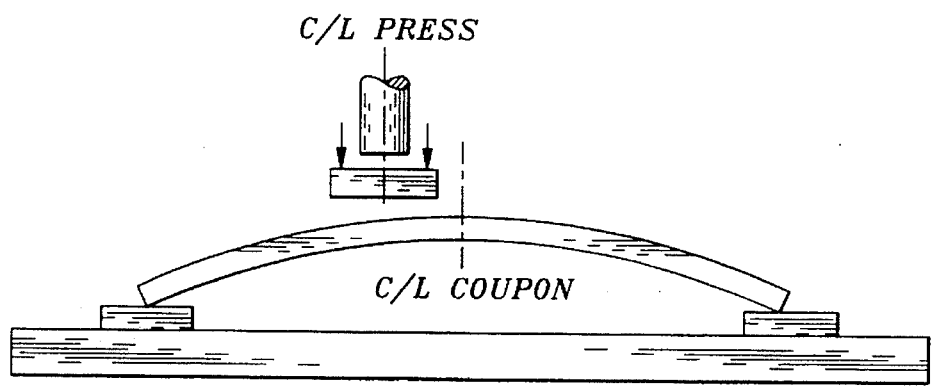
FIG. 8 is a schematic of pipe coupon processing.
Figure 9:
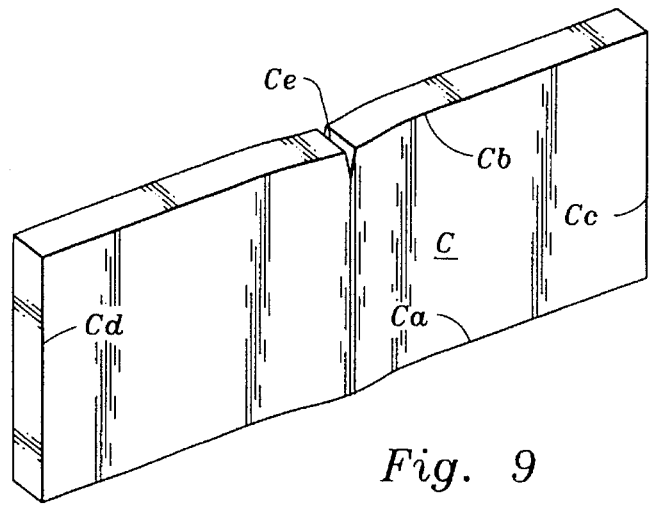
FIG. 9 is a further schematic of pipe coupon processing.

In use and operation, a coupon C is cut from a piece of pipe P preferably ninety degrees away from the pipe weld PW as shown in FIG. 7. It is to be noted that in many cases, the grain of the pipe runs parallel to the weld PW. It is desired in most cases to take a coupon C from the pipe such that the grain of the coupon is parallel to the direction of impact by the hammer during testing, although this is not mandatory. Note one 3"×24" coupon can be cut or one 6"×12" coupon is cut and thereafter recut to 3"×12". Once the coupon C has been cut from the pipe P (preferably with a torch), it may be bent as shown in FIG. 8 outboard a center line of the coupon C/L so as to not disturb the molecular structure at the area where the tear test is to be made. After some straightening, the edges of the coupon are trimmed with a fluid cooled cutting tool to remove any edge effect that may have occurred when cutting the coupon from the pipe using a torch. Next, a notch $C_e$ is placed on one longitudinal edge Cb of the coupon C.

Figure 10:
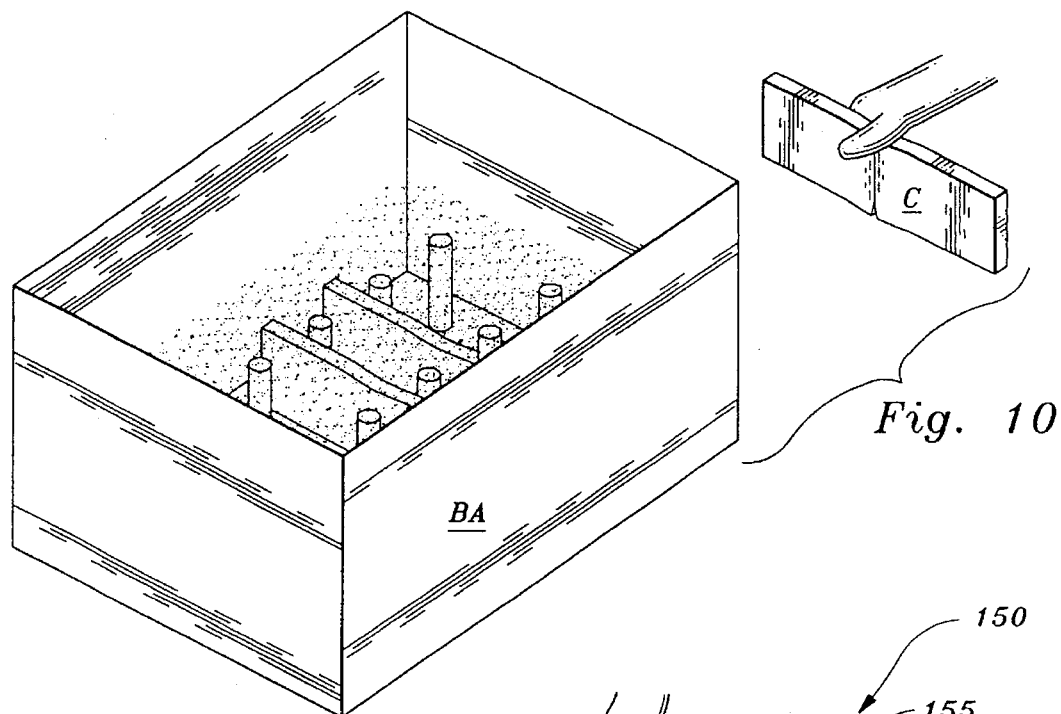
FIG. 10 depicts a step preparatory to testing.
Figure 14:
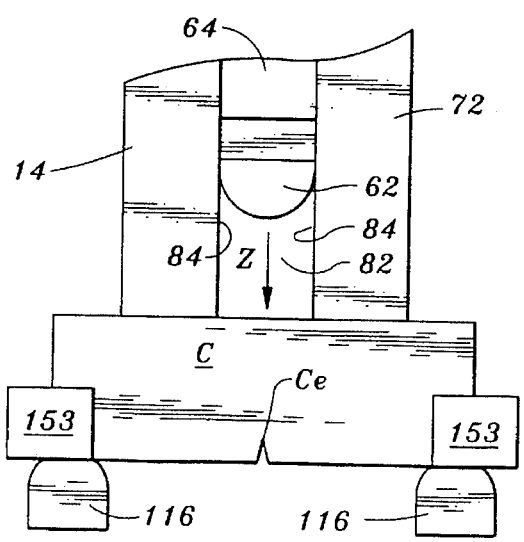
FIG. 14 is a view showing the coupon before fracture.
Figure 14A:
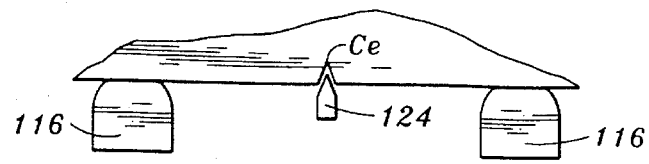
FIG. 14A is a view showing the coupon alignment.

FIG. 10 reflects that the coupon is next placed in a bath BA to maintain the coupon in a cold, brittle state, typically by immersion in alcohol which has been chilled with liquid nitrogen and maintained at a fixed temperature specified by pipe purchasers. FIG. 11 reflects that the coupon, having thus been chilled, is placed within the sled 130 for testing by aligning the notch $C_e$ upon the rail 124 (FIG. 14A). Note that (FIG. 14) at impact, the coupon C is supported only by anvils 116. The test shall take place within ten seconds from removal from the bath in accordance with the present day American Petroleum Institute standards.

Figure 12:
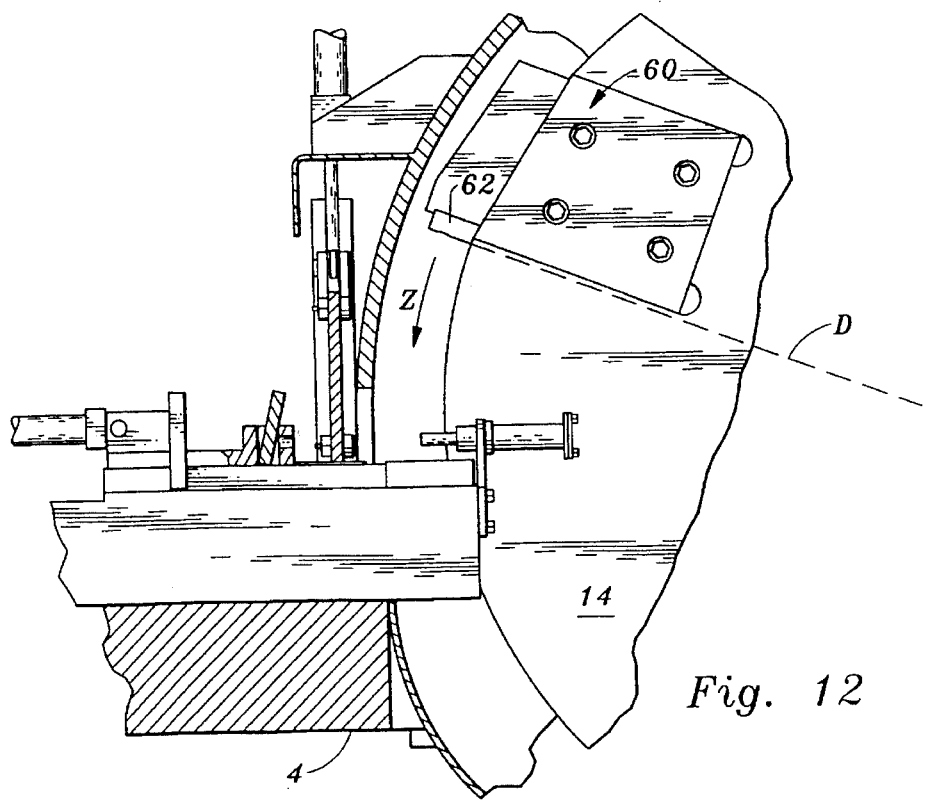
FIG. 12 is a side view prior to testing.

Referring to FIG. 12, the flywheel will have been spun to the desired velocity and sensors shall note exactly when the hammer has just gone beyond the carriage 90 (FIG. 13). At the same moment, the gate 152 will have been opened and the coupon C will be advanced into its testing position, with the coupon abutting against the pin 106 causing its retraction against tension of spring 108 in the sleeve 104. Hammer strike is shown in FIGS. 14 and 15. It is to be noted that the sled barrier 146 substantially occludes access to the coupon outside the device 10 of FIG. 15. The safety cage 400 provides a further margin of safety. FIG. 16 shows the coupon C having been severed into two portions being discharged out of the chute 198 in the lower cowl 190.

Figure 17:
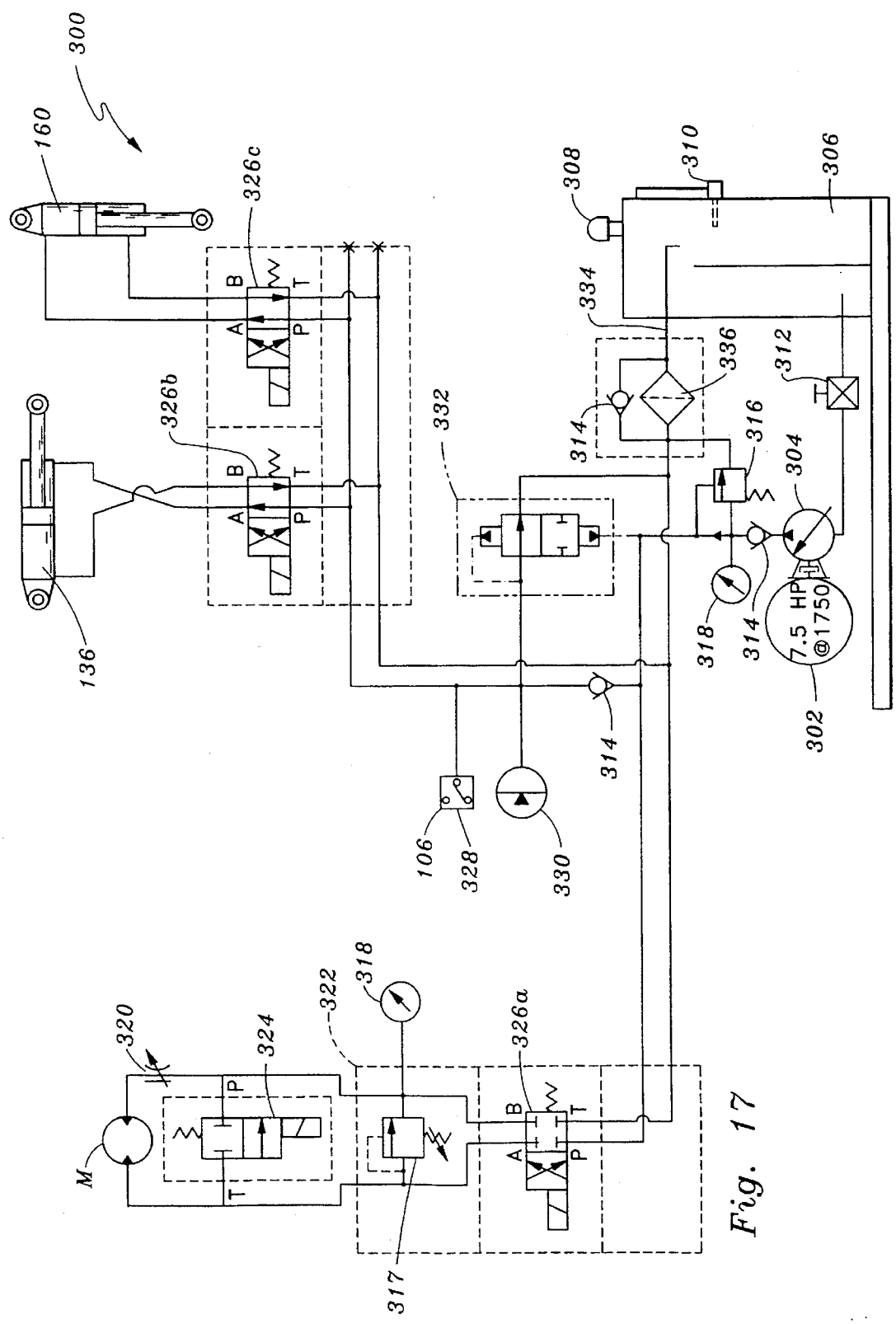
FIG. 17 is a schematic view of the hydraulic circuit.

Attention is now directed to FIG. 17 which reflects details of the hydraulic circuit 300 associated with the apparatus of the present invention. The purpose of the hydraulic circuit 300 is primarily to orchestrate the operation of three components mentioned hereinbefore: the motor M which powers the flywheel 14, the hydraulic cylinder 136 which moves the sled 130 and the associated coupon C, and the hydraulic cylinder 160 which controls the opening and closing of gate 152 that allows the coupon C to be advanced against the hammer 60.

An electric motor 302 powers a pump 304 to circulate hydraulic fluid contained within a reservoir 306 throughout the fluidic circuit 300. The reservoir 306 includes an access means 308 to allow replenishment of the fluid, and a sensor 310 which provides an indication of liquid level and/or temperature. Fluid passes from the reservoir 306 to the pump 304 by a gate valve 312. The downstream side of the pump 304 is protected by a check valve 314 and a relief valve 316 which, in conjunction with the reservoir 306 allows fluid to be diverted back into the reservoir 306. A pressure gauge 318 monitors the downstream side of the pump 304.

As mentioned supra, immediately prior to the hammer 60 contacting the coupon C, the hydraulic motor M will have been disengaged from its driving engagement with the electric motor 302 and pump 304. In this way, once divorced from operative powered communication with the pump 304, the hammer 60 will contact the coupon C solely by virtue of a known velocity imparted through the flywheel 14. Sensing means 200, accordingly, disengages the motor M immediately before the hammer 60 contacts the coupon C. When this occurs, fluid normally driving the motor M will have been diverted. The terminal velocity of the hammer via the motor M is controlled by a flow control 320 which preferably could be a variable pressure compensator. Fluid communicating with the motor M and pressure compensator flow control 320 pass through a relief module 322 which is monitored by a pressure gauge 318 and protected by a variable relief valve 317. The relief module 322 is in fluidic communication with a two position two-way hydraulic switch 324 which, when activated, diverts the hydraulic fluid past the motor. When the coupon C is to be fractured, the two position two-way hydraulic switch 324 and the three position four-way hydraulic valve 326a are actuated, thereby disallowing hydraulic fluid to flow to the motor M. As a result, the flywheel 14 is operating purely on its own quite substantial momentum.

The hydraulic cylinder 160 that opens the gate 152 is similarly coupled to a two position four-way valve 326c for opening and closing the gate 152 at the predetermined moment. Typically, once the position of the hammer 60 has been noted by sensing means 200 to have just passed the carriage area (FIG. 13) the hydraulic cylinder 160 will have been actuated moving the gate 152 in the direction of the arrow "W".

Concomitantly, upon the gate 152 opening as shown in FIG. 13, the coupon C will be advanced by actuation of the hydraulic cylinder 136 in the direction of the arrow "X" shown in FIG. 13. The hydraulic cylinder 136 of FIG. 17 is enabled by a two position four-way valve 326b. Pressure switch 328 is an electrical switch that closes when a preset hydraulic oil pressure is reached. The computer code is written such that valves 326b and 326c cannot energize unless pressure switch 328 is closed, This is done to ensure that sufficient pressure is present to fully actuate cylinders 136 arid 160 in the time required.

Because the extraordinary mass of the flywheel 14 requires a high torque motor M, and because the coupon C must be fractured within ten seconds of its having been removed from the cooling bath BA of FIG. 10, it is imperative that the system does not stall or slow down due to low hydraulic pressure. Yet at the same time, it is desired that hydraulic cylinders 136 and 160 not be needlessly oversized for their relatively low load requirements. Accordingly, an accumulator 330 is in operative communication with the hydraulic cylinders 136 and 160. The accumulator 330 is operatively coupled to a check valve 314 and also to an accumulator dump valve 332 which assures that hydraulic fluid will be stored with a sufficient volume for instant access and use by the hydraulic cylinders 136 and 160 as needed. As shown in the drawing, the accumulator dump valve 332 communicates back with the reservoir 306 via a return line 334. Note the return line 334 includes a filter bypass 314 and includes a filter 336.

Figure 24:
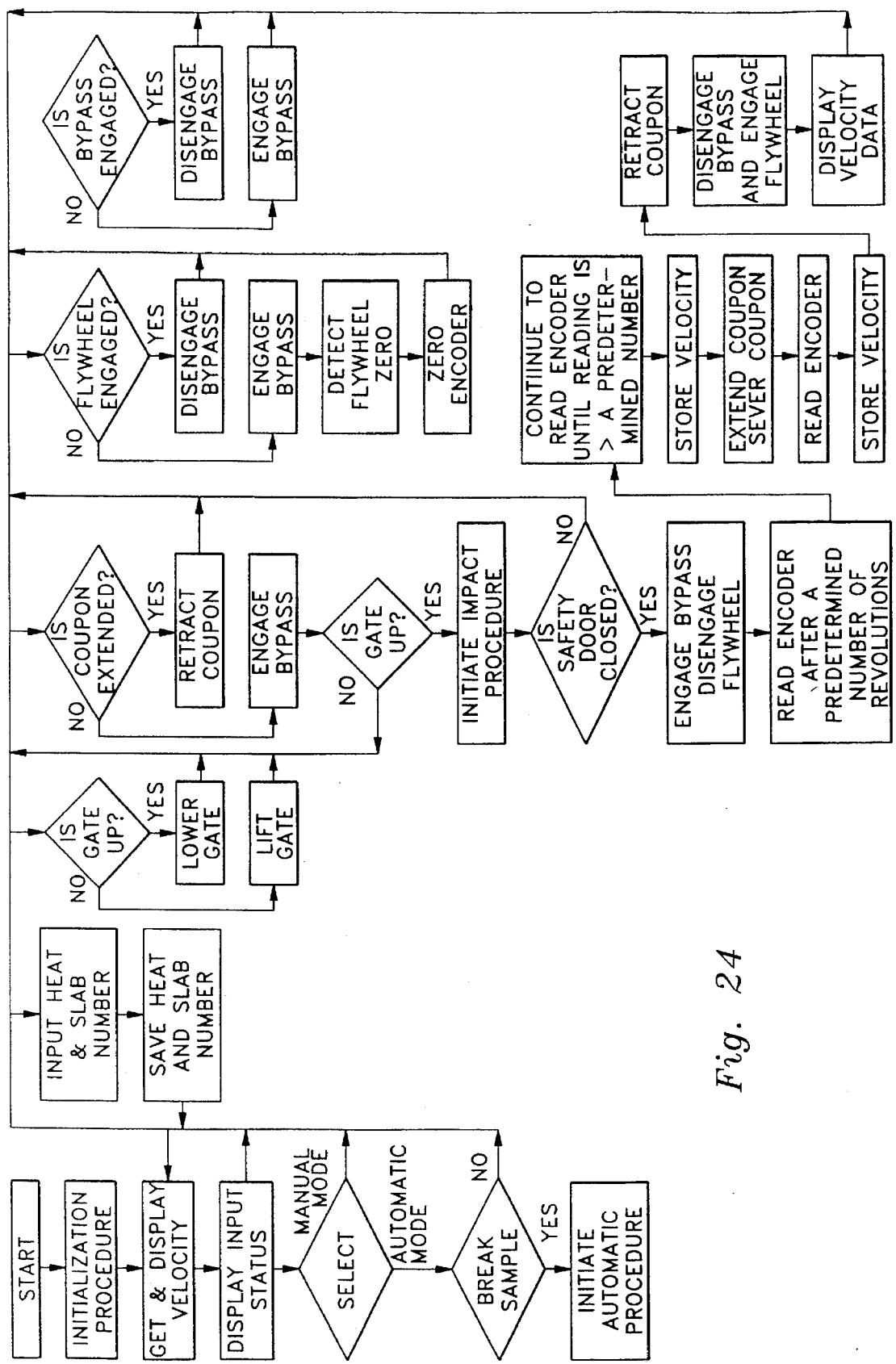
FIG. 24 is a block diagram of a procedure which is followed by a sensing means.

FIG. 24 is a block diagram, simplified for clarity, of the procedure which is followed by the sensing means 200 in order to promulgate the destructive testing of the coupon C. At the outset, a startup procedure is carried out in order to initialize the sensing means 200 (FIG. 193 which includes a computer 222 and the encoder 202. With this accomplished, the encoder 202 in conjunction with the computer 222 reads the velocity at which the flywheel 14 is traveling. The computer 222 translates and then displays this velocity to an operator.

Next the operator is prompted for an input status of the coupon testing apparatus 10 and is given a choice between an automatic mode or a manual mode of severing the coupon C. The automatic mode automatically initiates the severing of the coupon C using pre-programmed data stored in a memory means 225 of the computer 222. In contrast, the manual mode prompts the operator for input at various intervals throughout the procedure of severing the coupon C.

In the manual mode the operator is first prompted to input a heat number and a slab number of the coupon C for identification purposes. This information is saved in memory means 225 by the computer 222. The operator is then prompted as to whether or not the gate 152 is opened, the coupon C is extended, the flywheel 14 is engaged and a bypass is engaged.

Assuming the flywheel 14 is engaged, the gate 152 is opened and the coupon C is not extended, the next step would be to engage the bypass by actuating switch 324 and valve 326a. Once the bypass is engaged the hydraulic motor M will be disengaged from its driving engagement with the electric motor 302 and pump 304 (FIG. 17). At this time, the flywheel zero is detected and the encoder is zeroed.

A procedure to sever the coupon C is now initiated. The user is prompted one last time to insure that the safety door is closed. If the operator responds with a "yes" the sensing means 200 assures that the bypass is engaged and as a result the flywheel 14 is disengaged from the force applying means. The encoder 202 is read by the computer 222 after a predetermined number of revolutions of the flywheel 14 and this reading is continued until the reading is greater than a predetermined number. Once the predetermined number is reached the velocity of the flywheel 14 and hammer 60 is a known velocity and is stored in memory means 225 by the computer 222.

The sled 130 supporting the coupon C is then advanced into its testing position and the hammer 60 severs the coupon C. Immediately after the severing process of the coupon C the encoder 202 is read to determine a decrease in the known velocity of the flywheel 14. This velocity decrease is stored in memory means 225 by the computer 222. The computer 222 can then be used to provide the means for correlating the decrease in the known velocity with a shear force required to sever or tear the coupon C. The sled 130 is then retracted and the bypass is disengaged so that the motor can engage the flywheel 14 and spin it back to the desired velocity. At this time the sensing means 200 is ready for severing another coupon C.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for destructive testing of a coupon formed from metal, comprising, in combination:

a flywheel having an outer periphery, a hammer fixed to said flywheel and oriented to extend beyond said outer periphery thereby providing a hammer striking surface nose which orbits with said flywheel and said striking surface nose remains exposed beyond said flywheel, a carriage means, means for moving said carriage means from a first retracted position clear of said hammer striking surface to a second deployed position in a path of said hammer striking surface, coupon supporting means disposed on said carriage means, and sensing means allowing said coupon to be moved to said second deployed position, whereby in said second deployed position, said coupon is placed in the path of said hammer.

2. The apparatus of claim 1 wherein said carriage means includes a sled means having a cradle within which the coupon is supported, and orienting means on said carriage means for precisely locating the coupon both with respect to said cradle, said sled and said hammer.

3. The apparatus of claim 2 wherein said hammer is held in fixed relationship with respect to said flywheel and is fastened thereto by means of a hammer receiving anchor recess formed in said flywheel, a hammer anchor plate dimensioned to be received within said recess, said nose of said hammer operatively coupled to said hammer anchor plate and hammer retaining means fastening said hammer anchor plate and nose to said flywheel.

4. The apparatus of claim 3 wherein said hammer is located on a diagonal of said flywheel.

5. The apparatus of claim 4 wherein a shield overlies said flywheel and precludes the through passage of debris therebeyond, and a gate means is operatively coupled to said shield and interposed in a path of travel for the coupon from said first retracted position to said second deployed position, whereby said gate opens to allow access to an interior of said shield allowing the coupon to come into contact with said hammer.

6. The apparatus of claim 5 wherein said sensing means are operatively coupled to a means to advance said sled to said second deployed position from said first retracted position, said sensing means further coupled to said gate for allowing said gate to be opened allowing access beyond said shield in synchrony with said sled and means for disengaging a motor which powers said flywheel immediately prior to said hammer striking the coupon.

7. A pipe tester for determining the structural integrity of pipe by removing a coupon from a representative sample of pipe and destructively tear testing the coupon, comprising, in combination:

coupon support means, hammer means, hammer rotating and supporting means coupled to said hammer means to cause said hammer means to orbit outside of said rotating and supporting means at a known velocity, means for moving said coupon support means from a retracted area away from said hammer means into a path of and into contact with said hammer means once said hammer means reaches the known velocity, and means to disable said hammer powering means just prior to contacting the coupon.

8. The tester of claim 7 including means to sense a decrease in the known velocity during tear testing the coupon and means correlating the decrease in known velocity with a shear force required to tear the coupon.

9. The tester of claim 8 wherein said hammer powering means includes means for rotating said hammer means about an axis of rotation and means monitoring said hammer means about said axis of rotation for sensing the position of said hammer means.

10. The tester of claim 9 wherein said position sensing means is operatively coupled to said means for moving said coupon support to synchronize coupon motion with said position of said hammer means.

11. The tester of claim 10 wherein said coupon moving means includes a cradle provided with means for precisely locating said coupon with respect to said cradle and said hammer means.

12. The tester of claim 11 including a scatter shield circumscribing said hammer means and gate means allowing access to said hammer beyond said shield for said coupon and said coupon support means.

13. The tester of claim 12 including circuit means for controlling said hammer means, said means for moving said coupon support means and said gate means, and said shaft positioning means operatively communicating thereto.

14. A method for testing the structural integrity of material having a directional grain which correlates with a potential line of failure of the material, the steps including:

obtaining a specimen of the material to be tested, orienting the directional grain of the specimen so that the directional grain is exposed to a force in excess of that required for failure, rotating a force applying means including a hammer which is fixed to project out in an orbital path, moving the specimen into the orbital path of the hammer, and measuring the force required for the force applying means to pass through the specimen, thereby destroying the specimen.

15. The method of claim 14 including disengaging the force applying means from a source of power which provides the rotation of the force applying means immediately prior to having the specimen be contacted by the force applying means so that the measuring of the force required to pass through the specimen is a known speed devoid from any motive force other than momentum of the force applying means.

16. The method of claim 15 including surrounding the force applying means with a protective shield and orienting a gate in a path between the specimen and the force applying means, and opening the gate immediately prior to placing the specimen in contact with the force applying means.

17. The method of claim 6 including altering the ambient temperature of the specimen immediately prior to testing its structural integrity.

18. The method of claim 17 including sensing the position of the force applying means at all times and as a function of time so that its position and relative motion can be accurately measured.

19. The method of claim 18 including forming a locating notch on the specimen prior to testing, and orienting the specimen with respect to the force applying means such that the notch is in the path of travel of the force applying means and examining the specimen subsequent to the testing as to the characteristics of the mode of failure of the specimen.

20. The method of claim 19 including forming the force applying means as a flywheel and placing the hammer on an outer periphery of the flywheel and fixed on an outer periphery of the flywheel to be held in a single position during the testing and causing the specimen to come into contact with the hammer on the flywheel by moving the specimen from a first retracted position to a second deployed position in the path of the hammer.

21. A method for testing the structural integrity of material having a directional grain which correlates with a potential line of failure of the material, the steps including:

obtaining a specimen of the material to be tested, orienting the directional grain of the specimen so that the directional grain is exposed to a force in excess of that required for failure, rotating a force applying means, placing the specimen in the path of the force applying means, measuring the force required to pass through the specimen, disengaging the force applying means from a source of power which provides the rotation of the force applying means immediately prior to having the specimen be contacted by the force applying means so that the measuring of the force required to pass through the specimen is a known speed devoid from any motive force other than momentum of the force applying means, surrounding the force applying means with a protective shield and orienting a gate in a path between the specimen and the force applying means, and opening the gate immediately prior to placing the specimen in contact with the force applying means, and altering the ambient temperature of the specimen immediately prior to testing its structural integrity.

22. A method for testing the structural integrity of material having a directional grain which correlates with a potential line of failure of the material, the steps including:

obtaining a specimen of the material to be tested, orienting the directional grain of the specimen so that the directional grain is exposed to a force in excess of that required for failure, rotating a force applying means, placing the specimen in the path of the force applying means, measuring the force required to pass through the specimen and altering the ambient temperature of the specimen immediately prior to testing its structural integrity.

23. An apparatus for destructive testing of a coupon formed from metal, comprising, in combination:

a flywheel having an outer periphery, a hammer coupled to said flywheel and extending beyond said outer periphery, a carriage means, means for moving said carriage means from a first retracted position to a second deployed position, coupon supporting means disposed on said carriage means, means to alter the temperature of the coupon immediately prior to testing its structural integrity, and sensing means allowing said coupon to be moved to said second deployed position, whereby in said second deployed position, said coupon is placed in the path of said hammer.

24. A pipe tester for determining the structural integrity of pipe by removing a coupon from a representative sample of pipe and tear testing the coupon, comprising, in combination:

coupon support means, hammer means, hammer powering means coupled to said hammer means to cause said hammer means to achieve a known velocity, means for moving said coupon support means into contact with said hammer means once said hammer means reaches the known velocity, means to alter the temperature of the coupon immediately prior to testing its structural integrity, means to disable said hammer powering means just prior to contacting the coupon.

* * * * *